(12) United States Patent
Yang et al.

(10) Patent No.: US 11,493,889 B2
(45) Date of Patent: Nov. 8, 2022

(54) WEARABLE DEVICE

(71) Applicant: Huawei Technologies Co., Ltd., Shenzhen (CN)

(72) Inventors: Rongguang Yang, Shenzhen (CN); Shiyou Sun, Shenzhen (CN); Menglong Zhao, Shenzhen (CN); Bin Zhang, Shenzhen (CN); Guangsheng Liu, Shenzhen (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 410 days.

(21) Appl. No.: 16/493,680

(22) PCT Filed: May 23, 2017

(86) PCT No.: PCT/CN2017/085438
§ 371 (c)(1),
(2) Date: Sep. 12, 2019

(87) PCT Pub. No.: WO2018/129847
PCT Pub. Date: Jul. 19, 2018

(65) Prior Publication Data
US 2020/0233381 A1      Jul. 23, 2020

(30) Foreign Application Priority Data

Jan. 13, 2017  (CN) .......................... 201710025534.3

(51) Int. Cl.
*G04G 21/02*  (2010.01)
*A61B 5/0205* (2006.01)
(Continued)

(52) U.S. Cl.
CPC ....... *G04G 21/025* (2013.01); *A61B 5/02055* (2013.01); *A61B 5/681* (2013.01);
(Continued)

(58) Field of Classification Search
CPC ................ G04G 21/025; A61B 5/0205; A61B 5/02055; A61B 5/021; A61B 5/02416;
(Continued)

(56) References Cited

U.S. PATENT DOCUMENTS

| | | |
|---|---|---|
| 3,384,853 A | 5/1968 | Rademacher |
| 4,405,242 A | 9/1983 | Kosaka et al. |

(Continued)

FOREIGN PATENT DOCUMENTS

| | | |
|---|---|---|
| CN | 102196072 A | 9/2011 |
| CN | 202433698 U | 9/2012 |

(Continued)

OTHER PUBLICATIONS

Zhiqiang, L., "Heart rate detection on smart watches," Fujian Computer, vol. 6, 2014, 4 pages.

(Continued)

*Primary Examiner* — Christopher A Flory
(74) *Attorney, Agent, or Firm* — Conley Rose, P.C.

(57) ABSTRACT

A wearable device (100) includes a body (1) and a detection electrode (21). The body (1) includes an electrocardiosignal collection circuit (11), and an inner electrode (12) and an outer electrode (13) that are electrically connected to the electrocardiosignal collection circuit (11). The inner electrode (12) is configured to collect an electric potential signal of a first wearing position (200), and the outer electrode (13) is configured to collect an electric potential signal of a non-wearing position (300). The detection electrode (21) can move relative to the body (1), and the detection electrode (21) is configured to electrically connect to the electrocardiosignal collection circuit (11) and collect an electric potential signal of a second wearing position (400). The non-wearing position (300) and the second wearing position (400) are different from the first wearing position (200). The
(Continued)

wearable device (100) can measure electrocardiosignal data in time.

25 Claims, 16 Drawing Sheets

(51) Int. Cl.

| | | |
|---|---|---|
| A61B 5/00 | (2006.01) | |
| G04G 9/00 | (2006.01) | |
| H05K 1/02 | (2006.01) | |
| H05K 1/11 | (2006.01) | |
| H05K 1/18 | (2006.01) | |
| H05K 7/14 | (2006.01) | |
| A61B 5/021 | (2006.01) | |
| A61B 5/024 | (2006.01) | |
| A61B 5/282 | (2021.01) | |
| A61B 5/332 | (2021.01) | |
| A61B 5/339 | (2021.01) | |

(52) U.S. Cl.
CPC ........... *G04G 9/007* (2013.01); *H05K 1/0277* (2013.01); *H05K 1/115* (2013.01); *H05K 1/18* (2013.01); *H05K 7/1427* (2013.01); *A61B 5/021* (2013.01); *A61B 5/02416* (2013.01); *A61B 5/02438* (2013.01); *A61B 5/282* (2021.01); *A61B 5/332* (2021.01); *A61B 5/339* (2021.01); *A61B 5/6824* (2013.01); *A61B 2562/066* (2013.01); *A61B 2562/222* (2013.01); *A61B 2562/227* (2013.01); *H05K 2201/10151* (2013.01); *H05K 2201/10409* (2013.01)

(58) Field of Classification Search
CPC ..... A61B 5/02438; A61B 5/282; A61B 5/332; A61B 5/339; A61B 5/681; A61B 5/6824; A61B 2562/066; A61B 2562/222; A61B 2562/227; H05K 1/0277; H05K 1/115; H05K 2201/10151
See application file for complete search history.

(56) References Cited

U.S. PATENT DOCUMENTS

| | | | |
|---|---|---|---|
| 6,269,053 B1 | 7/2001 | Kawata et al. | |
| 10,485,475 B1* | 11/2019 | Miller | A61B 5/0059 |
| 2009/0301768 A1 | 12/2009 | Liu | |
| 2011/0221688 A1 | 9/2011 | Byun et al. | |
| 2015/0366469 A1 | 12/2015 | Harris et al. | |
| 2016/0029911 A1* | 2/2016 | Lee | A61B 5/681 |
| | | | 600/301 |
| 2016/0119664 A1 | 4/2016 | Straub et al. | |
| 2016/0270668 A1 | 9/2016 | Gil | |
| 2016/0338598 A1 | 11/2016 | Kegasawa | |
| 2016/0354036 A1 | 12/2016 | Jo et al. | |

FOREIGN PATENT DOCUMENTS

| | | |
|---|---|---|
| CN | 203059749 U | 7/2013 |
| CN | 203447277 U | 2/2014 |
| CN | 104665822 A | 6/2015 |
| CN | 204520675 U | 8/2015 |
| CN | 204856051 U | 12/2015 |
| CN | 204945633 U | 1/2016 |
| CN | 205041396 U | 2/2016 |
| CN | 105615870 A | 6/2016 |
| CN | 105960197 A | 9/2016 |
| CN | 106236051 A | 12/2016 |
| EP | 1043637 A2 | 10/2000 |
| EP | 3075312 A1 | 10/2016 |
| EP | 3099224 B1 | 5/2020 |
| JP | H08236878 A | 9/1996 |
| KR | 20110012784 A | 2/2011 |
| WO | 2016119664 A1 | 8/2016 |

OTHER PUBLICATIONS

Schuettler, M., et al., "Multichannel Neural Cuff Electrodes with Integrated Multiplexer Circuit," 1st Annual International IEEE-EMBS Special Topic Conference on Microtechnologies in Medicine and Biology, Proceedings (Cat. No. 00EX451), Oct. 12-14, 2000, pp. 624-629.
Foreign Communication From a Counterpart Application, Chinese Application No. 201780022927.7, Chinese Office Action dated Dec. 4, 2019, 9 pages.
Foreign Communication From a Counterpart Application, European Application No. 17891761.3, Extended European Search Report dated Oct. 11, 2019, 7 pages.
Foreign Communication From a Counterpart Application, PCT Application No. PCT/CN2017/085438, English Translation of International Search Report dated Oct. 17, 2017, 2 pages.
Foreign Communication From a Counterpart Application, PCT Application No. PCT/CN2017/085438, English Translation of Written Opinion dated Oct. 17, 2017, 6 pages.

* cited by examiner

WEARABLE DEVICE

CROSS-REFERENCE TO RELATED APPLICATIONS

This application is a national stage of International Application No. PCT/CN2017/085438, filed on May 23, 2017, which claims priority to Chinese Patent Application No. 201710025534.3, filed on Jan. 13, 2017. Both of the aforementioned applications are hereby incorporated by reference in their entireties.

TECHNICAL FIELD

This application relates to the field of electronic device technologies, and in particular, to a wearable device.

BACKGROUND

For some people who have a heart disease such as an electrocardiogram abnormality, the abnormality can be discovered in time only when electrocardiosignal data is detected in time, to prevent a possible lesion or a relapse as early as possible. Most conventional electrocardiogram (Electrocardiogram, ECG) measuring instruments are handheld all-in-one machines connected to clamp electrodes, suction chest electrodes, and tab electrodes by using lead wires. The conventional electrocardiogram measuring instrument in a large size is not easy to carry, and is mainly used in a scenario such as a hospital. Therefore, a purpose of in-time measurement cannot be achieved.

SUMMARY

To resolve a technical problem, embodiments of this application provide a wearable device that can measure electrocardiosignal data in time.

To achieve the foregoing objective, the embodiments of this application use the following technical solutions.

An embodiment of this application provides a wearable device. The wearable device may be configured to detect electrocardiosignal data of a user. The wearable device may be a smartwatch, a smart band, or the like. The wearable device includes a body and fittings. The body includes an electrocardiosignal collection circuit, and an inner electrode and an outer electrode that are electrically connected to the electrocardiosignal collection circuit. The inner electrode is configured to collect an electric potential signal of a first wearing position, and the outer electrode is configured to collect an electric potential signal of a non-wearing position. The non-wearing position is different from the first wearing position. The fittings include a detection electrode, and the detection electrode can move relative to the body. The detection electrode is configured to electrically connect to the electrocardiosignal collection circuit and collect an electric potential signal of a second wearing position. The second wearing position is different from the first wearing position. The electrocardiosignal collection circuit is configured to obtain the electrocardiosignal data of the user based on a potential difference between the electric potential signal of the first wearing position and the electric potential signal of the non-wearing position or a potential difference between the electric potential signal of the first wearing position and the electric potential signal of the second wearing position.

The wearable device has two usage states: In a first state, when the wearable device does not use the fittings, the inner electrode is worn in the first wearing position, the outer electrode is in contact with the non-wearing position, and the electrocardiosignal collection circuit is configured to obtain the electrocardiosignal data of the user based on the potential difference between the electric potential signal of the first wearing position and the electric potential signal of the non-wearing position. In a second state, when the wearable device uses the fittings, the inner electrode is worn in the first wearing position, the detection electrode is worn in the second wearing position, and the electrocardiosignal collection circuit is configured to obtain the electrocardiosignal data of the user based on the potential difference between the electric potential signal of the first wearing position and the electric potential signal of the second wearing position.

The body further includes a processing chip and a display screen. The processing chip is electrically connected to the electrocardiosignal collection circuit, and is configured to optimize the electrocardiosignal data. The display screen is electrically connected to the processing chip, and is configured to display the optimized electrocardiosignal data. The user can learn of the electrocardiosignal data of the user by viewing a displayed pattern (for example, an electrocardiogram waveform) on the display screen.

In this embodiment, because the wearable device is in a small size and is easy to carry, the user can wear the wearable device at any time, and measure real-time electrocardiosignal data of the user in time through cooperation between the inner electrode and the outer electrode or through cooperation between the inner electrode and the detection electrode, to detect a health status of the body in time.

It may be understood that the inner electrode and the outer electrode are fastened to the body, and the inner electrode and the outer electrode are used as stationary electrodes of the wearable device. When the user wears the body, the inner electrode is in continuous contact with the first wearing position. The user can measure the electrocardiosignal data provided that the user enables, based on a requirement, the non-wearing position to touch the outer electrode. The measurement action is active, convenient, and efficient. A stationary electrode has a very obvious emergency detection function in an emergency environment. The detection electrode can move relative to the body, and the detection electrode is used as an accessory electrode of the wearable device. After wearing the body and enabling the inner electrode to be in continuous contact with the first wearing position, the user may fasten the fittings to the second wearing position, so that the detection electrode is in continuous contact with the second wearing position. Therefore, the wearable device can continuously measure the electrocardiosignal data of the user, and continuously track a change in physiological indexes of the user, to better feed back a physical status of the user. As a wearable product, the accessory electrode can be used by the user in more scenarios (for example, in training or during sleep), to record continuous physiological indexes. Briefly, the wearable device in this embodiment not only can implement emergency detection on the electrocardiosignal data, but also can implement continuous detection on the electrocardiosignal data.

In an optional embodiment, the body includes a watch plate and a watch band connected to the watch plate. The watch plate includes a housing and a circuit board located inside the housing, and the circuit board is configured to bear the electrocardiosignal collection circuit.

In an optional embodiment, the housing includes a bottom wall and a side wall disposed around a periphery of the bottom wall, and the bottom wall is configured to be in contact with the first wearing position. The inner electrode is fastened to the bottom wall, to collect the electric potential signal of the first wearing position. The outer electrode is fastened to an end portion that is of the side wall and that is far away from the bottom wall, so that the non-wearing position of the user can be conveniently in contact with the outer electrode.

Optionally, the inner electrode is made of a stainless steel material having good corrosion resistance. The outer electrode is made of a stainless steel material having good corrosion resistance. The housing is made of a plastic material or a metal material. The housing is insulated from the inner electrode and the outer electrode.

In an implementation, the bottom wall is disposed with a first through hole. The watch plate further includes a fixed circuit board electrically connected to the circuit board. The fixed circuit board is disposed with a second through hole and a pad located on a periphery of the second through hole. The pad is electrically connected to the electrocardiosignal collection circuit by using the fixed circuit board and the circuit board.

Optionally, the inner electrode includes an electrode sheet and a connection base connected to the electrode sheet. The connection base is disposed with a connection hole, and a hole wall of the connection hole is disposed with an inner thread. The watch plate further includes a screw, and the screw is disposed with an outer thread matching the inner thread. The connection base extends into the first through hole. The screw is connected to the connection base after passing through the second through hole (where the inner thread is thread-connected to the outer thread). The screw locks the connection base and the fixed circuit board, so that the connection base is in contact with the pad. In this case, the electrode sheet is electrically connected to the electrocardiosignal collection circuit by using the connection base and the pad.

The connection base and the electrode sheet may be integrally formed, thereby simplifying a forming process of the inner electrode.

Optionally, the pad includes a first subpad and a second subpad that are disposed opposite to each other. The first subpad is disposed on a side that is of the fixed circuit board and that faces the connection base, and the first subpad is in contact with the connection base. The second subpad is disposed on a side that is of the fixed circuit board and that is far away from the connection base, and the second subpad is in contact with the screw. The screw is made of a conductive material, and is configured to enable the connection base to be electrically connected to the second subpad by using the screw. In this case, the electrode subset not only can be electrically connected to the electrocardiosignal collection circuit by using the connection base and the first subpad, but also can be electrically connected to the electrocardiosignal collection circuit by using the connection base, the screw, and the second subpad, so that the electrocardiosignal collection circuit can obtain a more accurate electric potential signal of the first wearing position.

Optionally, the watch plate further includes a waveform spring, the screw passes through the waveform spring, and the waveform spring is firmly pressed between the pad and the connection base. The waveform spring has preset pressure. The waveform spring is located between the fixed circuit board and the connection base. The screw passes through the waveform spring and locks the connection base, so that one surface of the waveform spring adheres to the connection base, and the other surface of the waveform spring adheres to the pad (the second subpad) of the fixed circuit board, thereby ensuring that a circuit between the electrode sheet and the fixed circuit board is reliably conducted. Therefore, the electrocardiosignal collection circuit can reliably collect an electric potential signal by using thinner electrode. In addition, the waveform spring has an anti-loose function, to prevent the inner electrode from becoming loose. The waveform spring may be welded to the pad.

Optionally, the watch plate further includes a sealing ring, and the sealing ring is firmly pressed between an outer wall of the connection base and a hole wall of the first through hole. Because the sealing ring is in a compressed state, the sealing ring can seal a gap between the outer wall of the connection base and the hole wall of the first through hole, thereby preventing moisture, dust, or the like from entering the housing through the first through hole, and therefore, a water resistance function and a dust-proof function are implemented.

The outer wall of the connection base is disposed with a first positioning step. The hole wall of the first through hole is disposed with a second positioning step. The first positioning step and the second positioning step are disposed opposite to each other. The sealing ring is disposed between the first positioning step and the second positioning step. The first positioning step and the second positioning step are configured to limit a position of the sealing ring, to prevent the sealing ring from becoming detached from the first through hole, and prevent the sealing ring from entering the housing or becoming detached from the housing.

Optionally, the bottom wall includes a central region and a peripheral region disposed around a periphery of the central region. The central region protrudes relative to the peripheral region, and the inner electrode is disposed in the central region, so that the inner electrode can be in better contact with the first wearing position, thereby improving quality of a detection signal of the inner electrode.

There may be at least two inner electrodes. The at least two inner electrodes are alternately disposed, to further improve quality of detection signals of the inner electrodes.

Optionally, the outer electrode includes a touch portion and a fixing portion connected to the touch portion. The touch portion is configured to be touched by the non-wearing position, so as to collect the electric potential signal of the non-wearing position. The end portion is disposed with a groove, and the fixing portion is engaged into the groove, so that the outer electrode is fastened to the housing. In this case, the touch portion abuts against an end surface that is of the side wall and that is far away from the bottom wall.

After the fixing portion is engaged into the groove, the fixing portion may be stuck to a wall of the groove by using a glue dispensing process, adhesive sticker, or the like, thereby improving reliability of a connection between the outer electrode and the housing. In addition, a cooperation structure between the fixing portion and the groove also increases a bond area between the outer electrode and the housing, so that the connection between the outer electrode and the housing is more reliable, thereby satisfying requirements of overall strength and water resistance of 50 m.

The watch plate further includes a first electrode spring and a flexible circuit board that are located inside the housing. One end of the first electrode spring extends into the groove to be connected to the fixing portion, the other end of the first electrode spring is connected to one end of the flexible circuit board, and the other end of the flexible circuit board is electrically connected to the electrocardiosignal collection circuit. The outer electrode is electrically connected to the electrocardiosignal collection circuit by using the first electrode sheet and the flexible circuit board. The end that is of the first electrode spring and that extends into the groove is firmly pressed between the fixing portion and the wall of the groove, so that the first electrode spring is in stable contact with the fixing portion, and a contact area is relatively large. Therefore, an electrical connection relationship between the first electrode sheet and the outer electrode is reliable. A connection region between the first electrode spring and the flexible circuit board may be fastened to the side wall by using a fastener, thereby preventing the first electrode spring and the flexible circuit board from moving away and becoming detached from each other, and ensuring a reliable connection between the first electrode spring and the flexible circuit board.

In another implementation, the watch plate further includes a second electrode spring and a connection circuit board. The second electrode spring is located inside the housing. The connection circuit board is located inside the housing and is electrically connected to the circuit board. The inner electrode is located on an outer side of the bottom wall. The bottom wall is disposed with a third through hole that directly faces the inner electrode. The second electrode spring passes through the third through hole and is firmly pressed between the inner electrode and the connection circuit board. The inner electrode is electrically connected to the circuit board sequentially by using the second electrode spring and the connection circuit board, thereby being electrically connected to the electrocardiosignal collection circuit.

Optionally, the bottom wall includes a central region and a peripheral region disposed around a periphery of the central region. The inner electrode is disposed in the peripheral region. The inner electrode may be a complete ring, or may be a plurality of arc-shaped segments that are alternately disposed.

The bottom wall is disposed with a concave installation slot. The inner electrode is built in the installation slot. A sealing ring may be disposed between an outer side face of the inner electrode and a wall of the installation slot, to prevent moisture and dust from entering the housing through the third through hole.

Optionally, the outer electrode includes a touch portion and a fixing portion connected to the touch portion. The touch portion is configured to be touched by the non-wearing position, so as to collect the electric potential signal of the non-wearing position. The fixing portion extends into the housing to be connected to the end.

The watch plate further includes a third electrode spring, and the third electrode spring is fastened to the connection circuit board and is elastically connected to the fixing portion. The outer electrode is electrically connected to the circuit board sequentially by using the third electrode spring and the connection circuit board, thereby being electrically connected to the electrocardiosignal collection circuit.

In an optional embodiment, the central region is disposed with a detection window and a transparent lens covering the detection window. The watch plate further includes a photoplethysmogram (PPG) disposed inside the housing. The photoplethysmogram is configured to detect a heart rate of the user by using the detection window. Because the detection window is disposed on the bottom wall of the housing, the detection window continuously directly faces the first wearing position, and the wearable device can continuously detect the heart rate of the user.

The watch plate further includes a sensor chip. The sensor chip is electrically connected to the photoplethysmogram and the processing chip, and is configured to transmit, to the processing chip, heart rate data of the user detected by the photoplethysmogram. The processing chip calculates and corrects a time difference between the electrocardiosignal data and the heart rate data based on the electrocardiosignal data and the heart rate data, to obtain a blood pressure value of the user. The wearable device can continuously detect the electrocardiosignal data and the heart rate data, and therefore, can continuously detect a fluctuation of blood pressure, to discover a problem of a blood pressure abnormality (for example, a common disease such as hypertension of people) in time, and can detect a health status of blood vessels (for example, vascular elasticity, a degree of vascular sclerosis, or whether a blood vessel is blocked).

In an optional embodiment, the watch band includes an inner side and an outer side that are disposed opposite to each other. The inner side is configured to be in contact with the first wearing position. The inner electrode is disposed on the inner side. The outer electrode is disposed on the outer side. The watch band is disposed with a second flexible circuit board. The inner electrode and the outer electrode are electrically connected to the circuit board by using the second flexible circuit board, thereby berg electrically connected to the electrocardiosignal collection circuit.

In this embodiment, the inner electrode and the outer electrode are fastened to the watch band, to simplify an inner structure of the watch plate, thereby reducing a size of the watch plate. This is beneficial to miniaturization of the wearable device.

In an optional embodiment, the fittings of the wearable device include a fixing band, a connector, and a cable connected between the fixing band and the connector. The detection electrode is disposed on an inner side of the fixing band. The fixing band is configured to fasten the detection electrode to the second wearing position. One end of the cable is electrically connected to the detection electrode, and the other end of the cable is electrically connected to the connector. The connector is detachably connected to the body.

In this embodiment, because the connector is detachably connected to the body, a detachable connection relationship also exists between the fittings and the body. The fittings may be connected to the body when continuous detection needs to be performed, and may be detached from the body when no continuous detection needs to be performed, so as to reduce a weight of the wearable device, thereby improving use flexability of the wearable device.

Optionally, the wearable device further includes a temperature detection electrode fastened to the fixing band, and the temperature detection electrode is electrically connected to the connector by using the cable. The temperature detection electrode is configured to detect a body temperature of the user, so that the wearable device can simultaneously detect the body temperature of the user. The temperature detection electrode is electrically connected to the processing chip. The processing chip can display the body temperature of the user on the display screen.

In an implementation, the connector is a plug. The body is disposed with a socket electrically connected to the electrocardiosignal collection circuit. The plug is detachably connected to the socket. The plug is connected to the socket by using a plug-in structure.

Optionally, the socket is disposed with a jack. A hole wall of the jack is disposed with a spring. The spring is configured to clamp the plug inserted into the jack, so that the plug can be stably plugged into the socket. In addition, the spring also has an electrical connection function.

Optionally, the plug is a USB (Universal Serial Bus, universal serial bus) plug or an earphone plug. The socket is a USB socket or an earphone jack matching the plug.

In another implementation, the connector is a magnetic head. The magnetic head is detachably adsorbed on the outer electrode. Specifically, the outer electrode is made of a metal material, and the magnetic head is disposed with a magnet, so that the magnetic head can be adsorbed on the outer electrode. The magnetic head and the outer electrode may be positioned by using a mortise and tenon connection (which is a connection manner for combining a mortise hole of one component and a tenon tongue of the other component).

DESCRIPTION OF EMBODIMENTS

Figure 1:
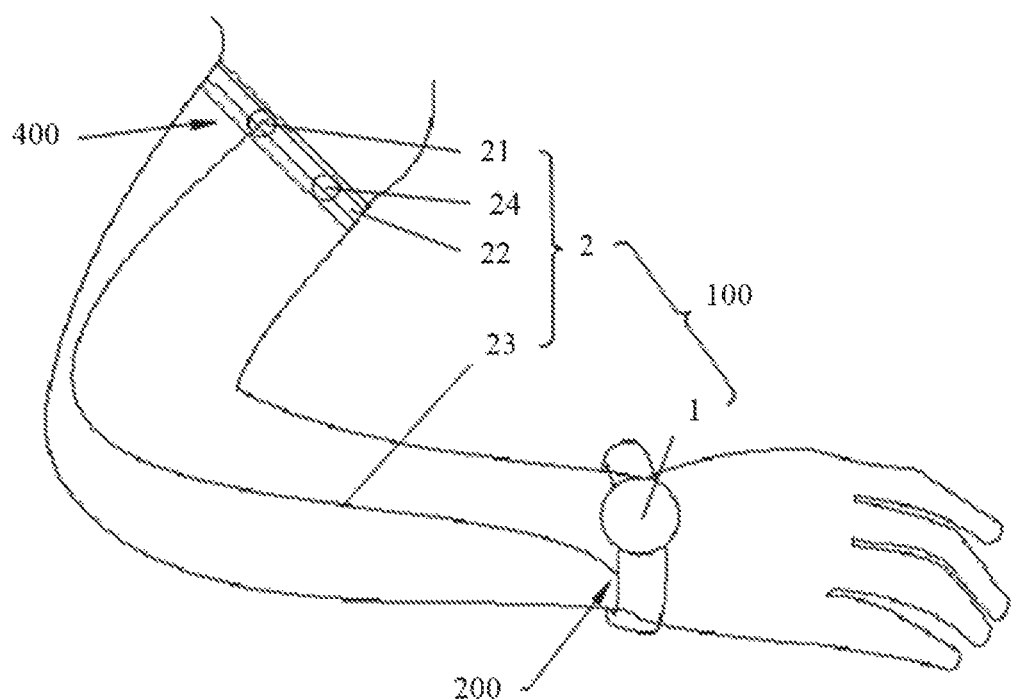
FIG. 1 is a first diagram of a usage state of a smartwatch according to an embodiment of this application.

The following describes the embodiments of this application with reference to the accompanying drawings in the embodiments of this application.

Referring to FIG. 1 to FIG. 7, this application discloses a wearable device. The wearable device may be configured to detect electrocardiosignal data of a user. The wearable device may be a smartwatch, a smart band, or the like. A smartwatch 100 is used as an example for description in this application.

The smartwatch 100 includes a body 1 and fittings 2. The body 1 includes an electrocardiosignal collection circuit 11, and an inner electrode 12 and an outer electrode 13 that are electrically connected to the electrocardiosignal collection circuit 11. The inner electrode 12 is configured to collect an electric potential signal of a first wearing position 200, and the outer electrode 13 is configured to collect an electric potential signal of a non-wearing position 300. The non-wearing position 300 is different from the first wearing position 200. The fittings 2 include a detection electrode 21, and the detection electrode 21 can move relative to the body 1. The detection electrode 21 is configured to electrically connect to the electrocardiosignal collection circuit 11 and collect an electric potential signal of a second wearing position 400. The second wearing position 400 is different from the first wearing position 200. The electrocardiosignal collection circuit 11 is configured to obtain electrocardiosignal data of a user based on a potential difference between the electric potential signal of the first wearing position 200 and the electric potential signal of the non-wearing position 300 or a potential difference between the electric potential signal of the first wearing position 200 and the electric potential signal of the second wearing position 400.

Figure 2:
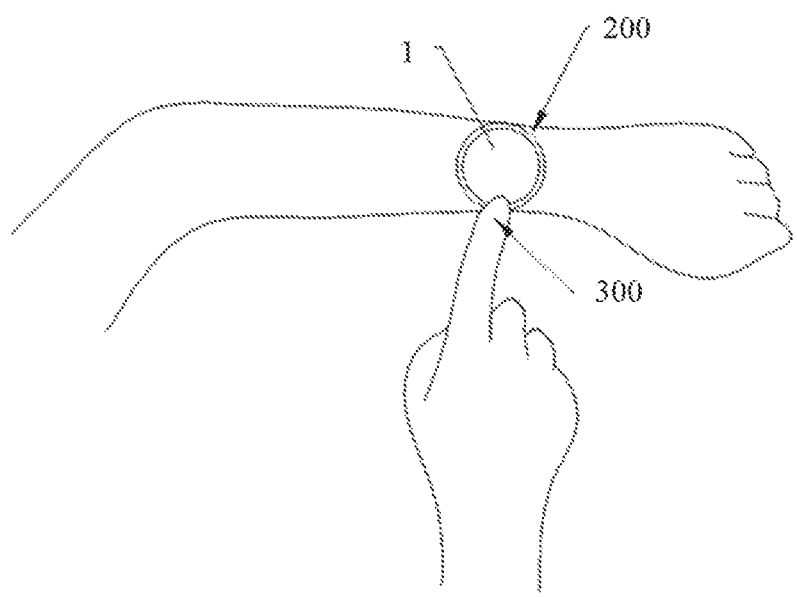
FIG. 2 is a second diagram of a usage state of the smartwatch shown in FIG. 1.

The smartwatch 100 has two usage states:

In a first state, as shown in FIG. 2, when the smartwatch 100 does not use the fittings 2, the inner electrode 12 is worn in the first wearing position 200, the outer electrode 13 is in contact with the non-wearing position 300, and the electrocardiosignal collection circuit 11 is configured to obtain the electrocardiosignal data of the user based on the potential difference between the electric potential signal of the first wearing position 200 and the electric potential signal of the non-wearing position 300. For example, the user wears the body 1 on a wrist on a wearing side, the first wearing position 200 may be the wrist on the wearing side of the user, and the inner electrode 12 collects an electric potential signal at the wrist on the wearing side of the user. A finger on a non-wearing side of the user is in contact with the outer electrode 13, the non-wearing position 300 may be the finger on the non-wearing side of the user, and the outer electrode 13 collects an electric potential signal at the finger on the non-wearing side of the user. The electrocardiosignal collection circuit 11 obtains the electrocardiosignal data of the user based on a potential difference between the electric potential signal collected by the inner electrode 12 and the electric potential signal collected by the outer electrode 13.

In a second state, as shown in FIG. 1, when the smartwatch 100 uses the fittings 2, the inner electrode 12 is worn in the first wearing position 200, the detection electrode 21 is worn in the second wearing position 400, and the electrocardiosignal collection circuit 11 is configured to obtain the electrocardiosignal data of the user based on the potential difference between the electric potential signal of the first wearing position 200 and the electric potential signal of the second wearing position 400. For example, the user wears the body 1 on a wrist on a wearing side, the first wearing position 200 is the wrist on the wearing side of the user, and the inner electrode 12 collects an electric potential signal at the wrist on the wearing side of the user. The detection electrode 21 is fastened to an arm on the wearing side of the user, the second wearing position 400 is the arm on the wearing side of the user, and the detection electrode 21 collects an electric potential signal at the arm on the wearing side of the user. The electrocardiosignal collection circuit 11 obtains the electrocardiosignal data of the user based on a potential difference between the electric potential signal collected by the inner electrode 12 and the electric potential signal collected by the detection electrode 21.

The first wearing position 200 may be usually the wrist on which the user wears the body 1. The non-wearing position 300 may be a hand (such as fingers or a palm), a chest (where the user may raise the wrist on the wearing side, so that the outer electrode 13 touches the chest of the user), a leg, or the like on which the user does not wear the body 1. The second wearing position 400 may be the arm of the wrist on which the user wears the body 1, thereby facilitating daily activities of the user. Certainly, the second wearing position 400 may alternatively be another position different from the first wearing position 200, for example, a chest, a leg, or the like.

The body 1 further includes a processing chip 14 and a display 15. The processing chip 14 is electrically connected to the electrocardiosignal collection circuit 11, and is configured to process the electrocardiosignal data. The processing chip 14 may set a software filtering algorithm, a display optimization algorithm, or the like. The display 15 is electrically connected to the processing chip 14, and is configured to display the optimized electrocardiosignal data. The user can learn of the electrocardiosignal data of the user by viewing a displayed pattern (for example, an electrocardiogram waveform) on the display 15. The electrocardiosignal collection circuit 11 may be carried by a chip or a circuit board. The display 15 may be a touch display.

In this embodiment, because the smartwatch 100 is in a small size and is easy to carry, the user can wear the smartwatch 100 at any time, and measure real-time electrocardiosignal data of the user in time through cooperation between the inner electrode 12 and the outer electrode 13 or through cooperation between the inner electrode 12 and the detection electrode 21, to detect a health status of the body in time.

It may be understood that the inner electrode 12 and the outer electrode 13 are fastened to the body 1, and the inner electrode 12 and the outer electrode 13 are used as stationary electrodes of the smartwatch 100. When the user wears the body 1, the inner electrode 12 is in continuous contact with the first wearing position 200. The user can measure the electrocardiosignal data provided that the user enables, based on a requirement, the non-wearing position 300 to touch the outer electrode 13. The measurement action is active, convenient, and efficient. A stationary electrode has a very obvious emergency detection function in an emergency environment. The detection electrode 21 can move relative to the body 1, and the detection electrode 21 is used as an accessory electrode of the smartwatch 100. After wearing the body 1 and enabling the inner electrode 12 to be in continuous contact with the first wearing position 200, the user may fasten the fittings 2 to the second wearing position 400, so that the detection electrode 21 is in continuous contact with the second wearing position 400. Therefore, the smartwatch 100 can continuously measure the electrocardiosignal data of the user, and continuously track a change in physiological indexes of the user, to better feed back a physical status of the user. As a wearable product, the accessory electrode can be used by the user in more scenarios (for example, in training or during sleep), to record continuous physiological indexes. Briefly, the smartwatch 100 in this embodiment not only can implement emergency detection on the electrocardiosignal data, but also can implement continuous detection on the electrocardiosignal data.

Figure 3:
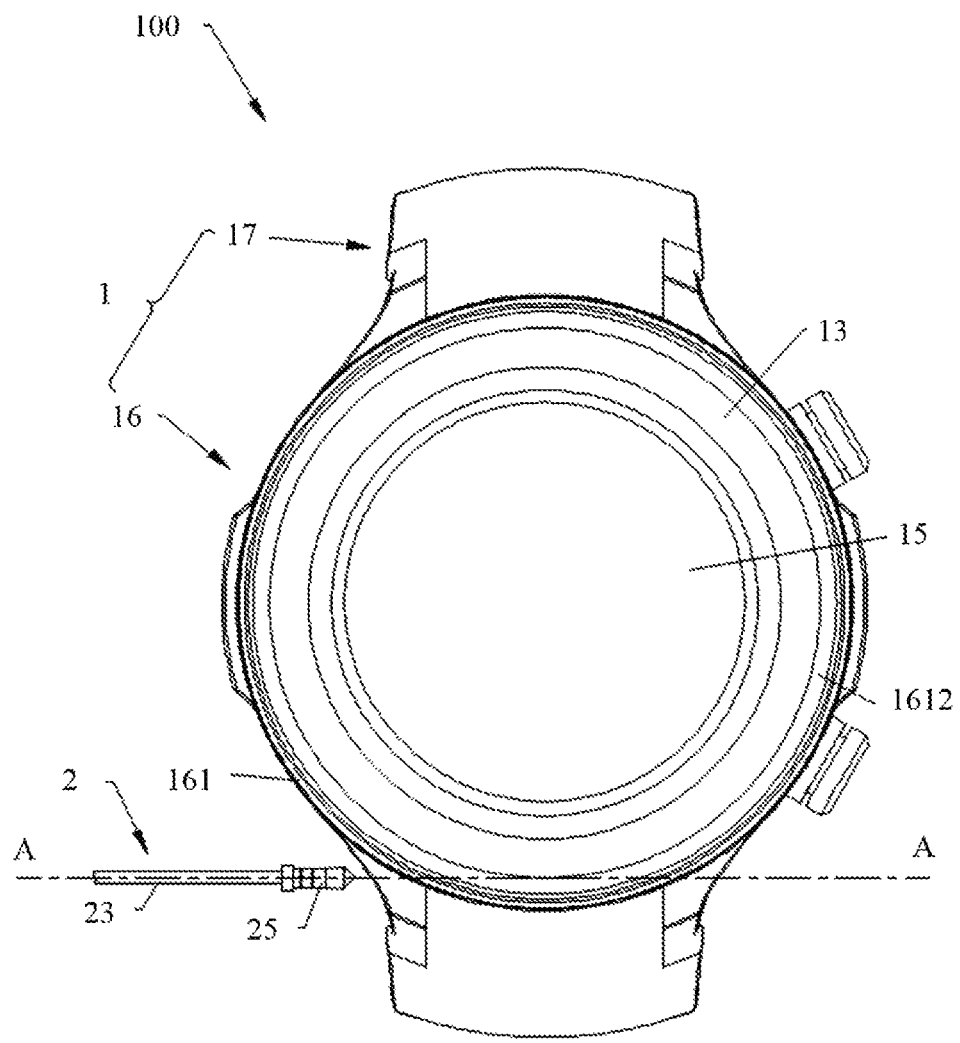
FIG. 3 is a top view of an implementation of the smartwatch shown in FIG. 1.
Figure 5:
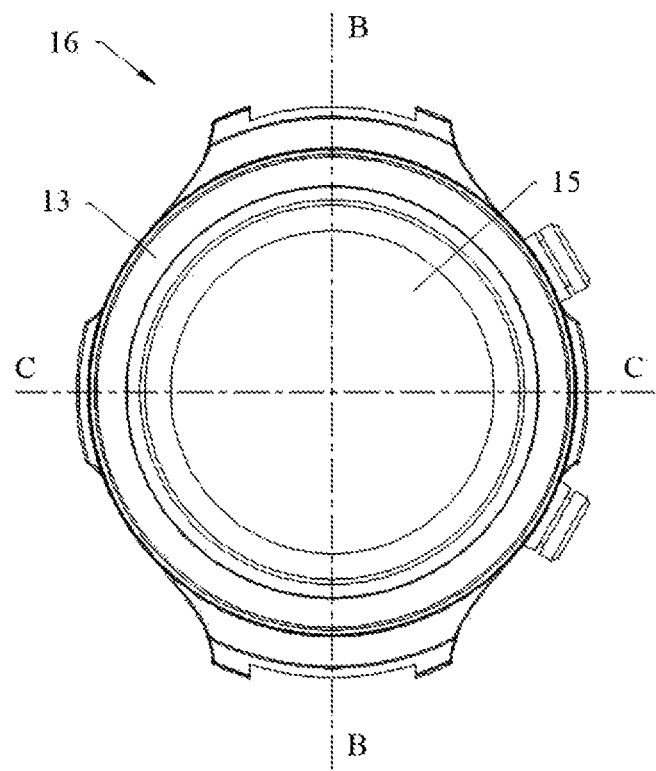
FIG. 5 is a top view of an implementation of a watch plate of the smartwatch shown in FIG. 3.
Figure 6:
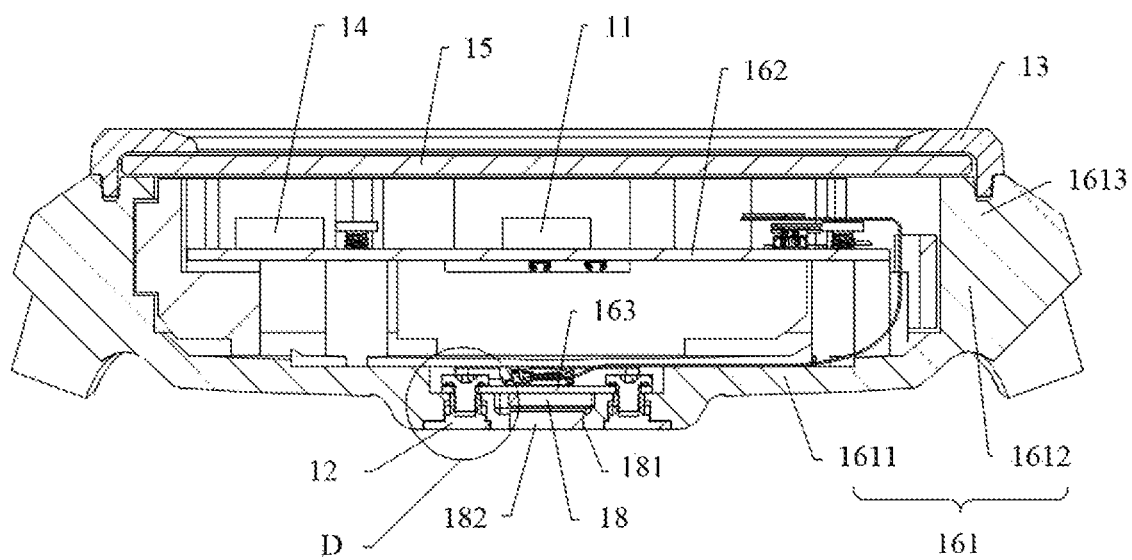
FIG. 6 is a sectional view of a structure of the watch plate shown in FIG. 5 in a B-B position.
Figure 7:
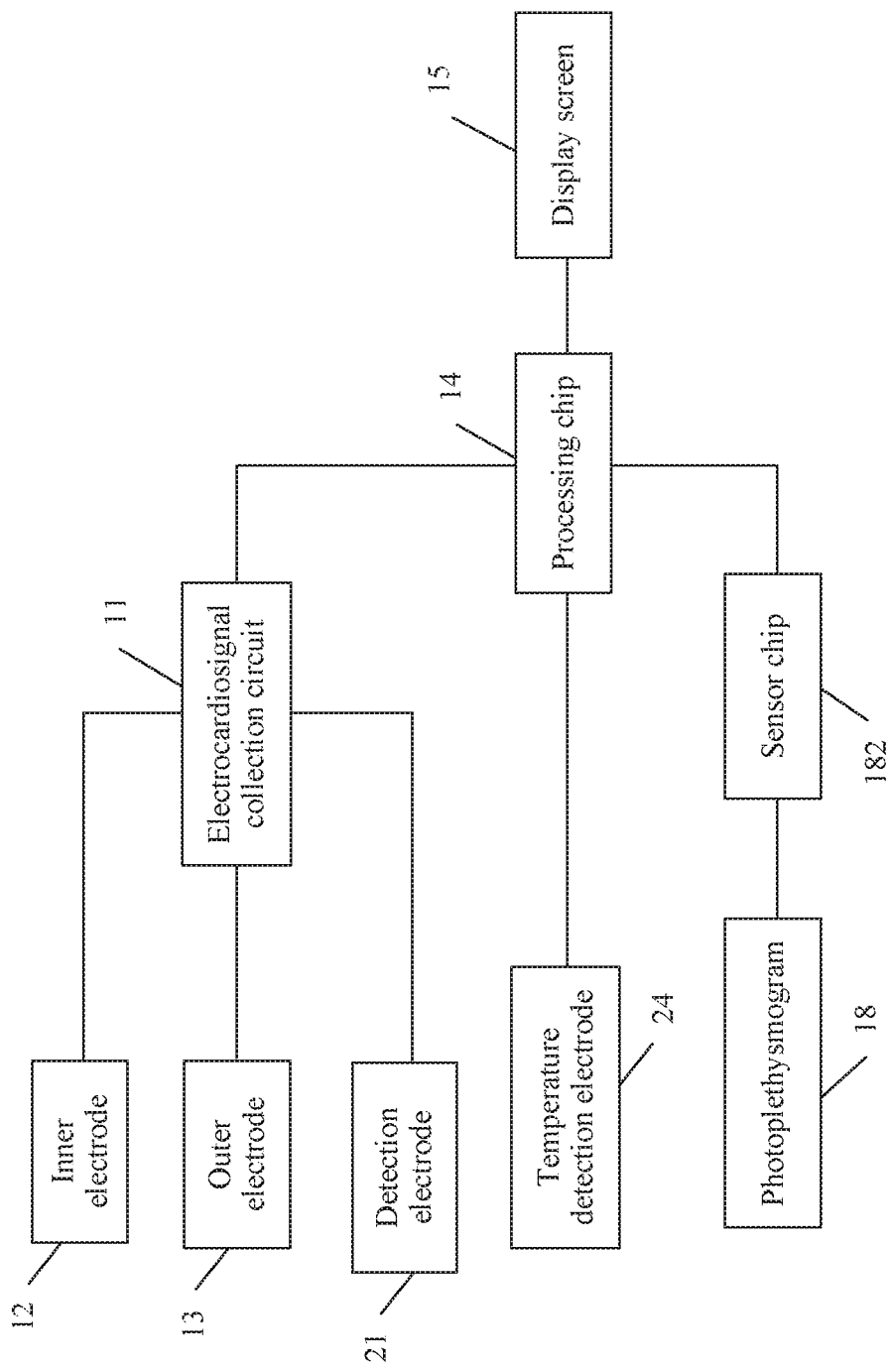
FIG. 7 is a schematic block diagram of a part of a structure connection relationship of the smartwatch shown in FIG. 1.
Figure 8:
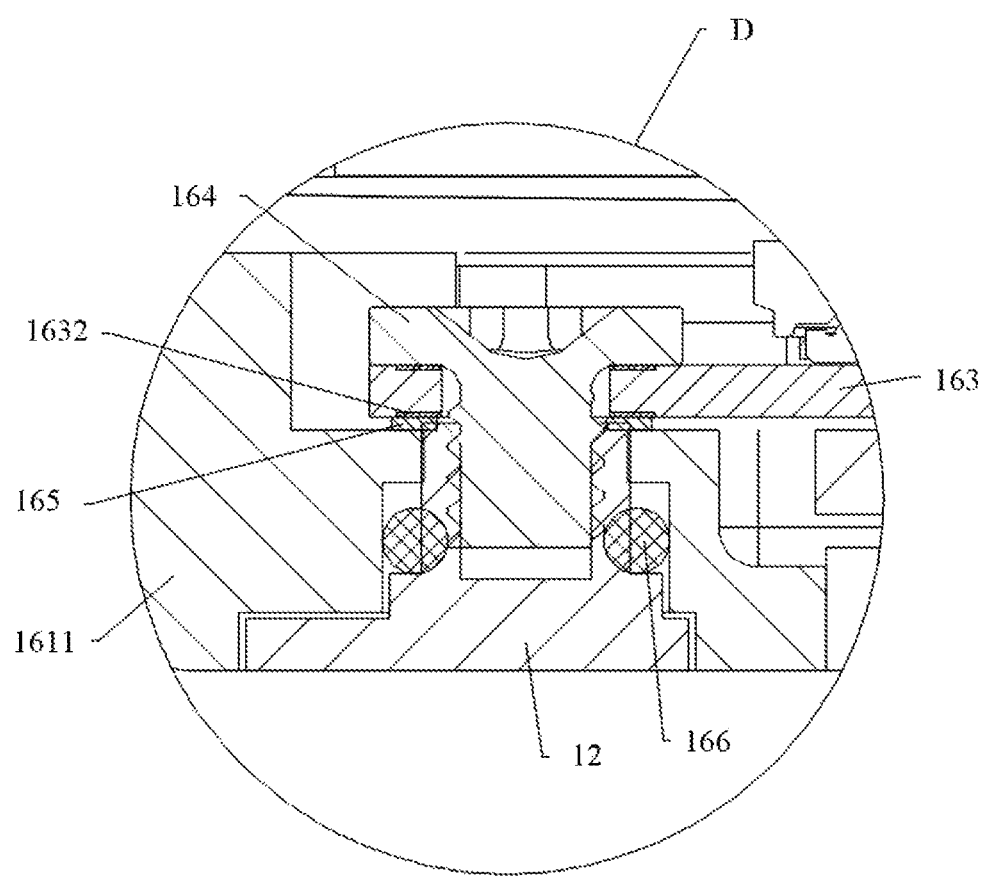
FIG. 8 is an enlarged schematic diagram of a structure in a position D in FIG. 6.
Figure 9:
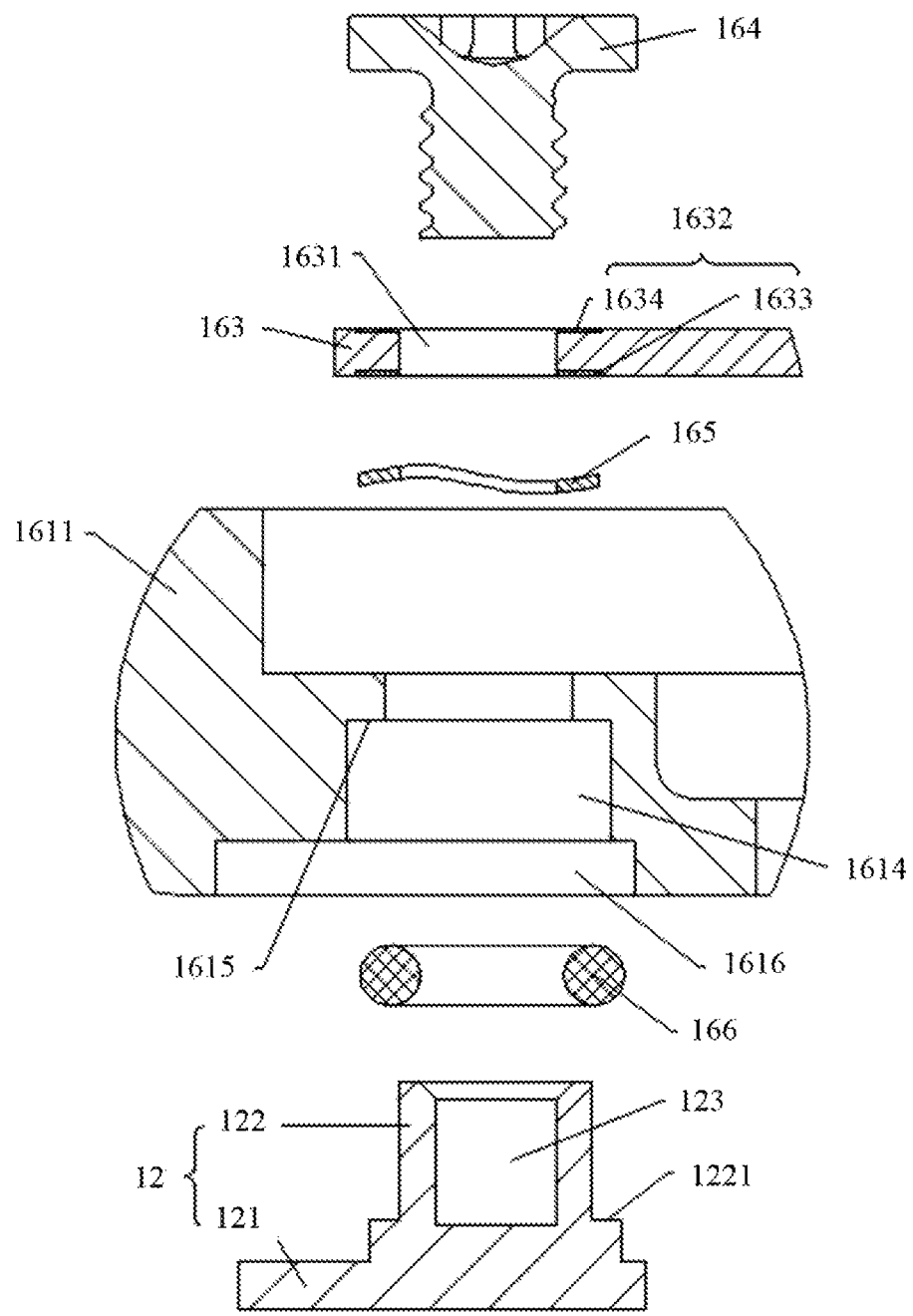
FIG. 9 is an exploded diagram of a part of a structure in FIG. 8.
Figure 10:
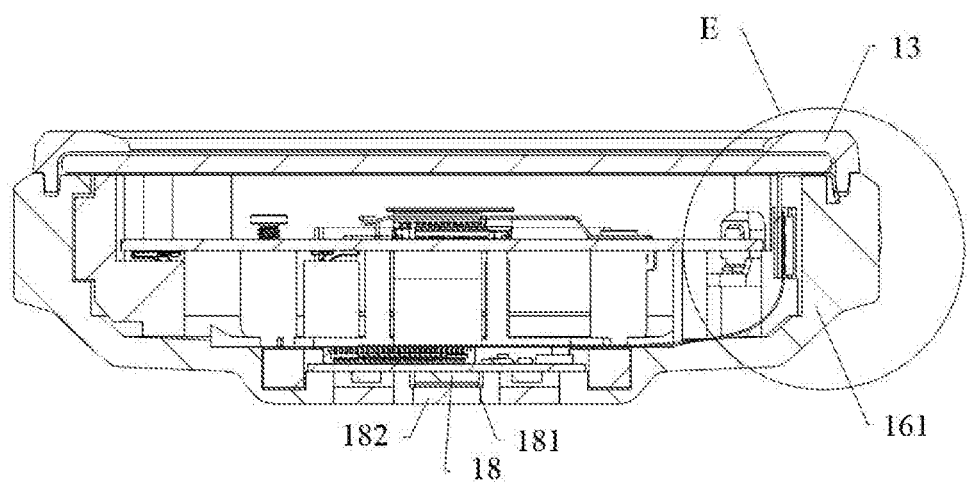
FIG. 10 is a sectional view of a structure of the watch plate shown in FIG. 5 in a C-C position.
Figure 11:
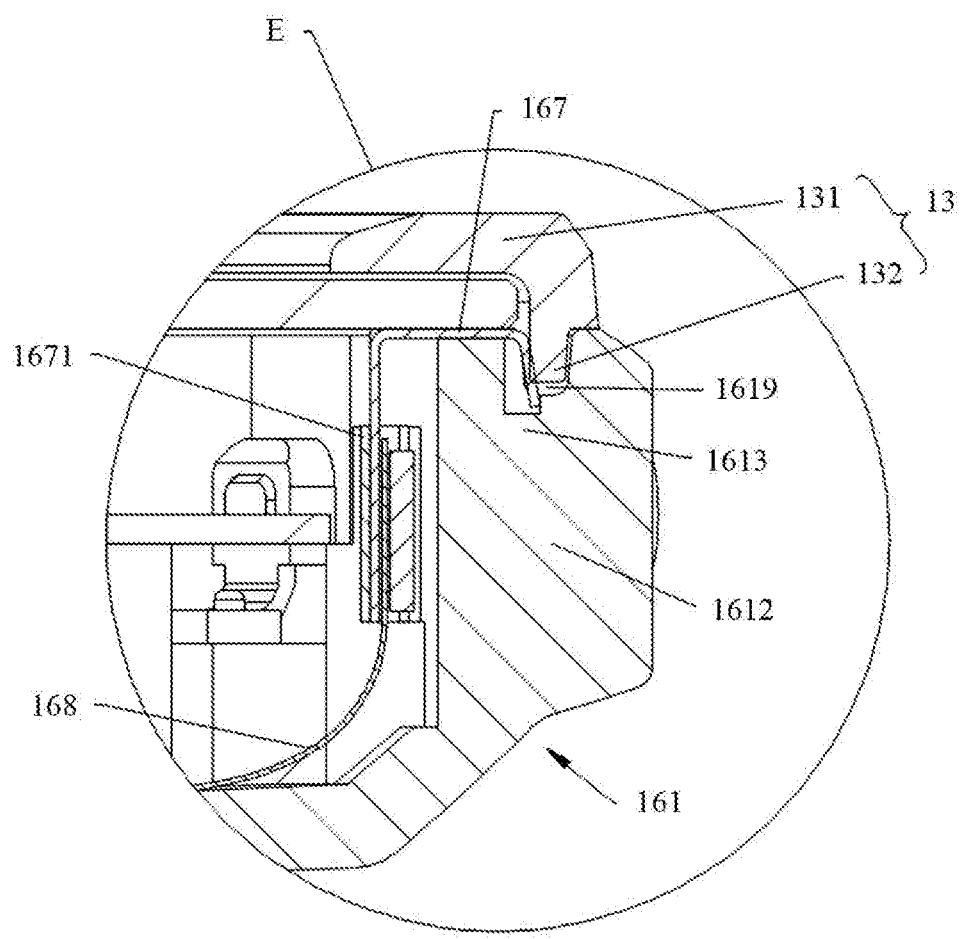
FIG. 11 is an enlarged schematic diagram of a structure in a position E in FIG. 10.
Figure 12:
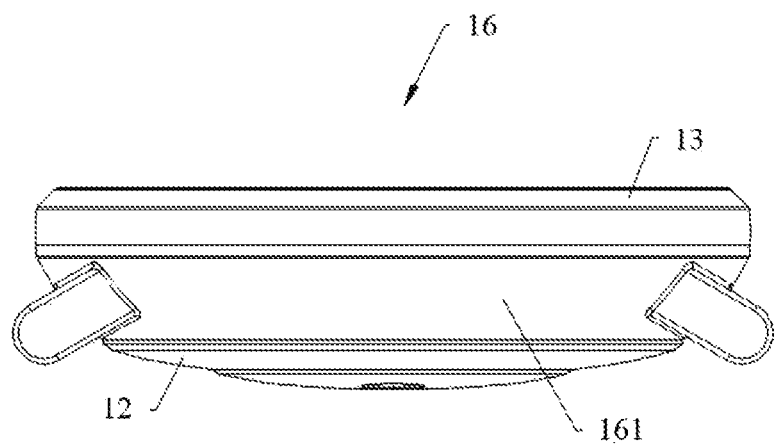
FIG. 12 is a front view of another implementation of a watch plate of the smartwatch shown in FIG. 3.

Referring to FIG. 3, FIG. 5, and FIG. 6, in an optional embodiment, the body 1 includes a watch plate 16 and a watch band 17 connected to the watch plate 16. The watch plate 16 includes a housing 161 and a circuit board 162 located inside the housing 161. The circuit board 162 is configured to bear the electrocardiosignal collection circuit 11. In an implementation, the processing chip 14 and a chip that is configured to bear the electrocardiosignal collection circuit 11 are disposed on the circuit board 162. In another implementation, the electrocardiosignal collection circuit 11 is directly formed on the circuit board 162. The display 15 is fastened to the housing 161.

Optionally, the housing 161 and the watch band 17 are integrally formed, to simplify a manufacturing process. In another implementation, the housing 161 and the watch band 17 may alternatively be fastened by using lugs or screws.

Referring to FIG. 1 to FIG. 17, in an optional embodiment, the housing 161 includes a bottom wall 1611 and a side wall 1612 disposed around a periphery of the bottom wall 1611, and the bottom wall 1611 is configured to be in contact with the first wearing position 200. In this case, the display 15 and the bottom wall 1611 may be disposed opposite to each other, and the side wall 1612 is connected between the display 15 and the bottom wall 1611.

The inner electrode 12 is fastened to the bottom wall 1611, to collect the electric potential signal of the first wearing position 200. The outer electrode 13 is fastened to an end 1613 that is of the side wall 1612 and that is far away from the bottom wall 1611, so that the non-wearing position 300 of the user can be conveniently in contact with the outer electrode 13.

Optionally, the inner electrode 12 is made of a stainless steel material having good corrosion resistance. The outer electrode 13 is made of a stainless steel material having good corrosion resistance. The housing 161 is made of a plastic material or a metal material. The housing 161 is insulated from the inner electrode 12 and the outer electrode 13. In another implementation, the inner electrode 12 and the outer electrode 13 may alternatively be made of other metal materials having corrosion resistance.

Referring to FIG. 1 to FIG. 11, in an implementation, the bottom wall 1611 is disposed with a first through hole 1614. The watch plate 16 further includes a fixed circuit board 163 electrically connected to the circuit board 162. The fixed circuit board 163 is disposed with a second through hole 1631 and a pad 1632 located on a periphery of the second through hole 1631. The pad 1632 is electrically connected to the electrocardiosignal collection circuit 11 by using the fixed circuit board 163 add the circuit board 162. The fixed circuit board 163 may be connected to the circuit board 162 by using a flexible circuit board. The fixed circuit board 163 and the flexible circuit board may be connected by using a ZIF (Zero Insertion Force, zero insertion force) connector or a BTB (Board to board, board to board) connector, and the flexible circuit board and the circuit board 162 may be connected by using a ZIF connector or a BTB connector.

Optionally, the inner electrode 12 includes an electrode sheet 121 and a connection base 122 connected to the electrode sheet 121. The connection base 122 is disposed with a connection hole 123, and a hole wall of the connection hole 123 is disposed with an inner thread. The watch plate 16 further includes a screw 164, and the screw 164 is disposed with an outer thread matching the inner thread. The connection base 122 extends into the first through hole 1614.

The screw 164 is connected to the connection base 122 after passing through the second through hole 1631 (where the inner thread is thread-connected to the outer thread). The screw 164 locks the connection base 122 and the fixed circuit board 163, so that the connection base 122 is in contact with the pad 1632. In this case, the electrode sheet 121 is electrically connected to the electrocardiosignal collection circuit 11 by using the connection base 122 and the pad 1632.

The connection base 122 and the electrode sheet 121 may be integrally formed, thereby simplifying a forming process of the inner electrode 12.

Optionally, the pad 1632 includes a first subpad 1633 and a second subpad 1634 that are disposed opposite to each other. The first subpad 1633 is disposed on a side that is of the fixed circuit board 163 and that faces the connection base 122, and the first subpad 1633 is in contact with the connection base 122. The second subpad 1634 is disposed on a side that is of the fixed circuit board 163 and that is far away from the connection base 122, and the second subpad 1634 is in contact with the screw 164. The screw 164 is made of a conductive material, and is configured to enable the connection base 122 to be electrically connected to the second subpad 1634 by using the screw 164. In this case, the electrode sheet 121 not only can be electrically connected to the electrocardiosignal collection circuit 11 by using the connection base 122 and the first subpad 1633, but also can be electrically connected to the electrocardiosignal collection circuit 11 by using the connection base 122, the screw 164, and the second subpad 1634, so that the electrocardiosignal collection circuit 11 can obtain a more accurate electric potential signal of the first wearing position 200. Certainly, in another implementation, the pad 1632 of the fixed circuit board 163 may be disposed with only the first subpad 1633.

Optionally, the watch plate 16 further includes a waveform spring 165, the screw 164 passes through the waveform spring 165, and the waveform spring 165 is firmly pressed between the pad 1632 and the connection base 122. Specifically, the waveform spring 165 has preset pressure. The waveform spring 165 is located between the fixed circuit board 163 and the connection base 122. The screw 164 passes through the waveform spring 165 and locks the connection base 122, so that one surface of the waveform spring 165 adheres to the connection base 122, and the other surface of the waveform spring 165 adheres to the pad 1632 (the second subpad 1634) of the fixed circuit board 163, thereby ensuring that a circuit between the electrode sheet 121 and the fixed circuit board 163 is reliably conducted. Therefore, the electrocardiosignal collection circuit 11 can reliably collect an electric potential signal by using the inner electrode 12. In addition, the waveform spring 165 has an anti-loose function, to prevent the inner electrode 12 from becoming loose. The waveform spring 165 may be welded to the pad 1632.

Optionally, the watch plate 16 further includes a sealing ring 166. The sealing ring 166 is firmly pressed between an outer wall of the connection base 122 and a hole wall of the first through hole 1614. Because the sealing ring 166 is in a compressed state, the sealing ring 166 can seal a gap between the outer wall of the connection base 122 and the hole wall of the first through hole 1614, thereby preventing moisture, dust, or the like from entering the housing 161 through the first through hole 1614, and therefore, a water resistance function and a dust-proof function are implemented.

The outer wall of the connection base 122 is disposed with a first positioning step 1221. The hole wall of the first through hole 1614 is disposed with a second positioning step 1615. The first positioning step 1221 and the second positioning step 1615 are disposed opposite to each other. The sealing ring 166 is disposed between the first positioning step 1221 and the second positioning step 1615. The first positioning step 1221 and the second positioning step 1615 are configured to limit a position of the sealing ring 166, to prevent the sealing ring 166 from becoming detached from the first through hole 1614, and prevent the sealing ring 166 from entering the housing 161 or becoming detached from the housing 161.

Optionally, the bottom wall 1611 is further disposed with an installation groove 1616 that is connected to the first through hole 1614, and the installation groove 1616 is on an outer surface of the bottom wall. When the connection base 122 extends into the first through hole 1614, the electrode sheet 121 is accommodated in the installation groove 1616. In a direction perpendicular to an axis of the first through hole 1614, an area of the installation groove 1616 is greater than an area of the first through hole 1614, and an area of the electrode sheet 121 is greater than an area of the connection base 122. A bottom wall of the installation groove 1616 is configured to perform position limiting on the electrode sheet 121, so as to position an installation position of the inner electrode 12, and prevent the inner electrode 12 from completely entering the housing 161.

Optionally, the bottom wall 1611 includes a central region 1617 and a peripheral region 1618 disposed around a periphery of the central region 1617. The central region 1617 protrudes relative to the peripheral region 1618, and the inner electrode 12 is disposed in the central region 1617, so that the inner electrode 12 can be in better contact with the first wearing position 200, thereby improving quality of a detection signal of the inner electrode 12.

There may be at least two inner electrodes 12. The at least two inner electrodes 12 are alternately disposed, to further improve quality of detection signals of the inner electrodes 12.

Optionally, the outer electrode 13 includes a touch portion 131 and a fixing portion 132 connected to the touch portion 131. The touch portion 131 is configured to be touched by the non-wearing position 300, so as to collect the electric potential signal of the non-wearing position 300. The end 1613 of the side wall 1612 is disposed with a groove 1619, and the fixing portion 132 is engaged into the groove 1619, so that the outer electrode 13 is fastened to the housing 161. In this case, the touch portion 131 abuts against an end surface that is of the side wall 1612 and that is far away from the bottom wall 1611.

After the fixing portion 132 is engaged into the groove 1619, the fixing portion 132 may be stuck to a wall of the groove 1619 by using a glue dispensing process, adhesive sticker, or the like, thereby improving reliability of a connection between the outer electrode 13 and the housing 161. In addition, a cooperation structure between the fixing portion 132 and the groove 1619 also increases a bond area between the outer electrode 13 and the housing 161, so that the connection between the outer electrode 13 and the housing 161 is more reliable, thereby satisfying requirements of overall strength and water resistance of 50 m.

The watch plate 16 further includes a first electrode spring 167 and a flexible circuit board 168 that are located inside the housing 161. One end of the first electrode spring 167 extends into the groove 1619 to be connected to the fixing portion 132, the other end of the first electrode spring 167 is connected to one end of the flexible circuit board 168, and the other end of the flexible circuit board 168 is electrically connected to the electrocardiosignal collection circuit 11. The outer electrode 13 is electrically connected to the electrocardiosignal collection circuit 11 by using the first electrode spring 167 and the flexible circuit board 168. The end that is of the first electrode spring 167 and that extends into the groove 1619 is firmly pressed between the fixing portion 132 and the wall of the groove 1619, so that the first electrode spring 167 is in stable contact with the fixing portion 132, and a contact area is relatively large. Therefore, an electrical connection relationship between the first electrode spring 167 and the outer electrode 13 is reliable. A connection region between the first electrode spring 167 and the flexible circuit board 168 may be fastened to the side wall 1612 by using a fastener 1671, thereby preventing the first electrode spring 167 and the flexible circuit board 168 from moving away and becoming detached from each other, and ensuring a reliable connection between the first electrode spring 167 and the flexible circuit board 168. The flexible circuit board 168 can be configured to connect to both the fixed circuit board 163 and the circuit board 162.

Referring to FIG. 1 to FIG. 4 and FIG. 12 to FIG. 17, in another implementation, the watch plate 16 further includes a second electrode spring 169 and a connection circuit board 163'. The second electrode spring 169 is located inside the housing 161. The connection circuit board 163' is located inside the housing 161 and is electrically connected to the circuit board 162. The inner electrode 12 is located on an outer side of the bottom wall 1611. The bottom wall 1611 is disposed with a third through hole 1614' that directly faces the inner electrode 12. The second electrode spring 169 passes through the third through hole 1614' and is firmly pressed between the inner electrode 12 and the connection circuit board 163'. The inner electrode 12 is electrically connected to the circuit board 162 sequentially by using the second electrode spring 169 and the connection circuit board 163', thereby being electrically connected to the electrocardiosignal collection circuit 11.

Optionally, the connection circuit board 163' may be a rigid circuit board or a flexible circuit board. When the connection circuit board 163' is a rigid circuit board, the connection circuit board 163' is electrically connected to the circuit board 162 by using a flexible circuit board. The flexible circuit board and the circuit board 162 may be connected by using a ZIF connector or a BTB connector. When the connection circuit board 163' is a flexible circuit board, the connection circuit board 163' may be directly connected to the circuit board 162. The connection circuit board 163' and the circuit board 162 may be connected by using a ZIF connector or a BTB connector.

Figure 13:
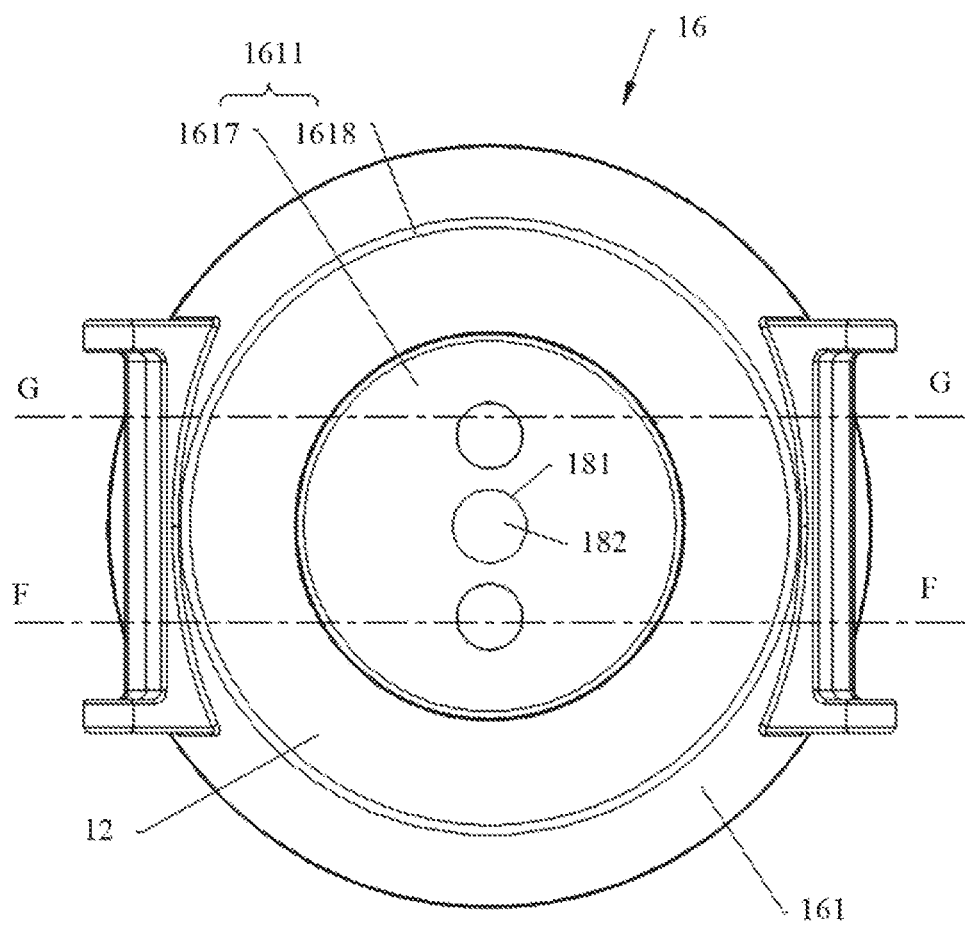
FIG. 13 is a bottom view of the watch plate shown in FIG. 12.
Figure 14:
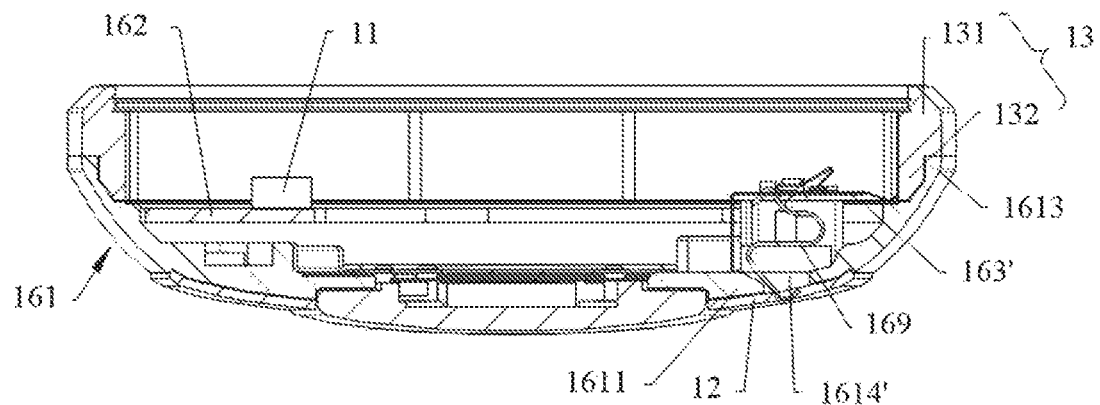
FIG. 14 is a sectional view of a structure of the watch plate shown in FIG. 13 in an F-F position.
Figure 15:
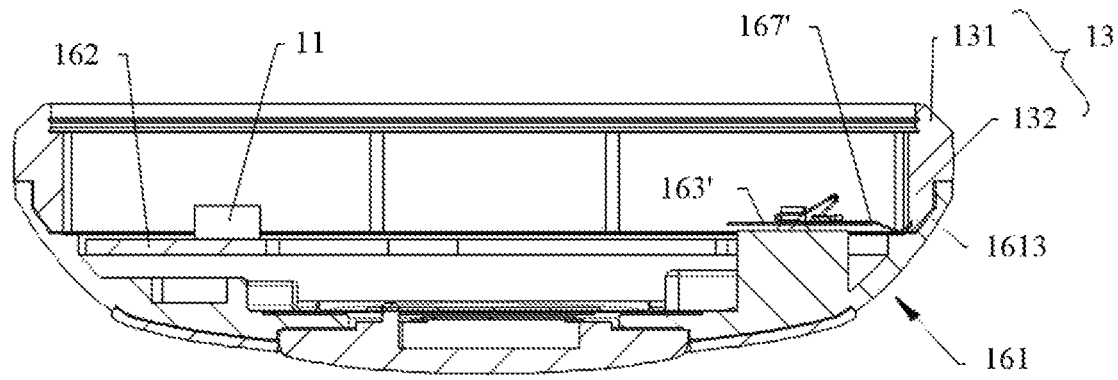
FIG. 15 is a sectional view of a structure of the watch plate shown in FIG. 13 in a G-G position.
Figure 16:
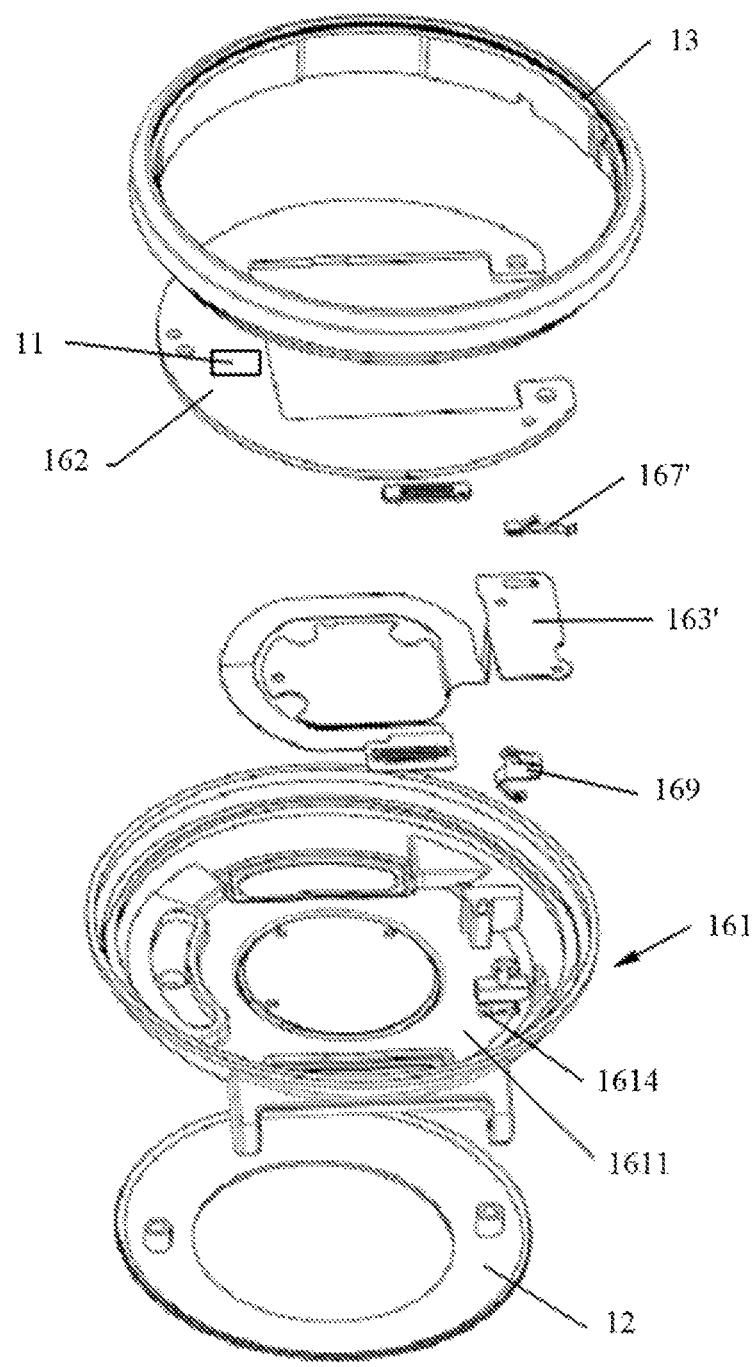
FIG. 16 is an exploded diagram of a part of a structure of the watch plate shown in FIG. 13.
Figure 17:
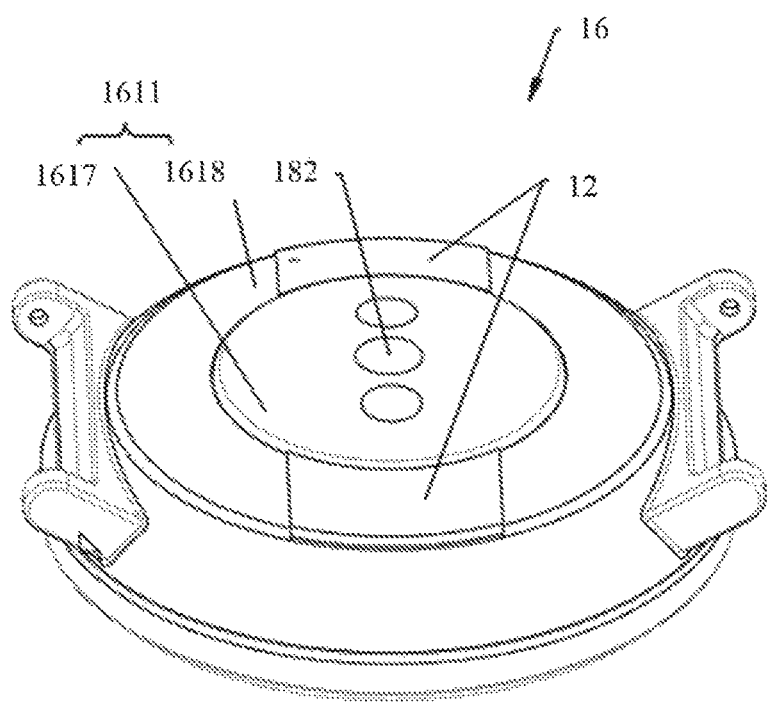
FIG. 17 is a schematic structural diagram of still another implementation of a watch plate of the smartwatch shown in FIG. 3.
Figure 18:
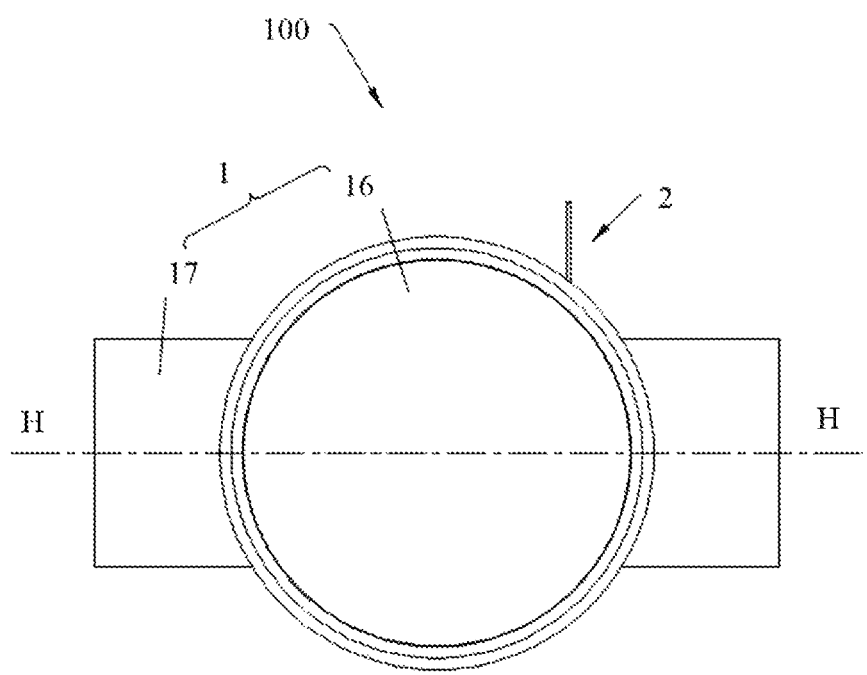
FIG. 18 is a top view of another implementation of the smartwatch shown in FIG. 1.
Figure 19:
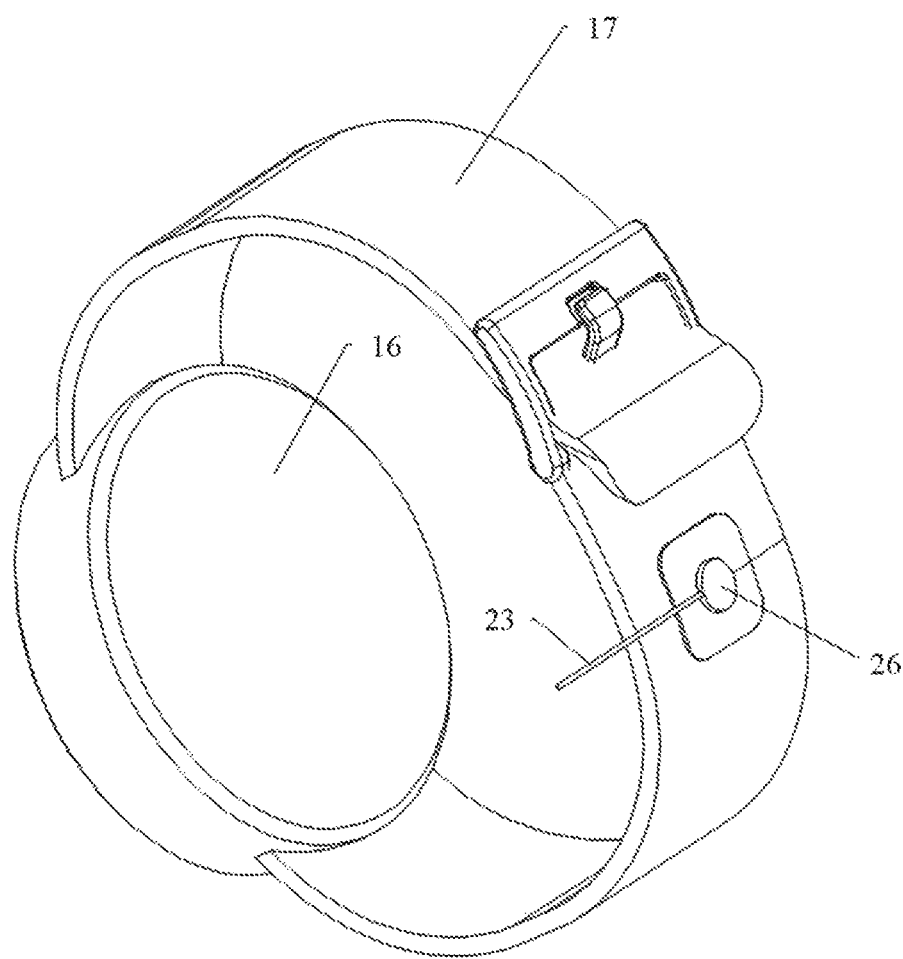
FIG. 19 is a stereogram of the smartwatch shown in FIG. 18.
Figure 20:
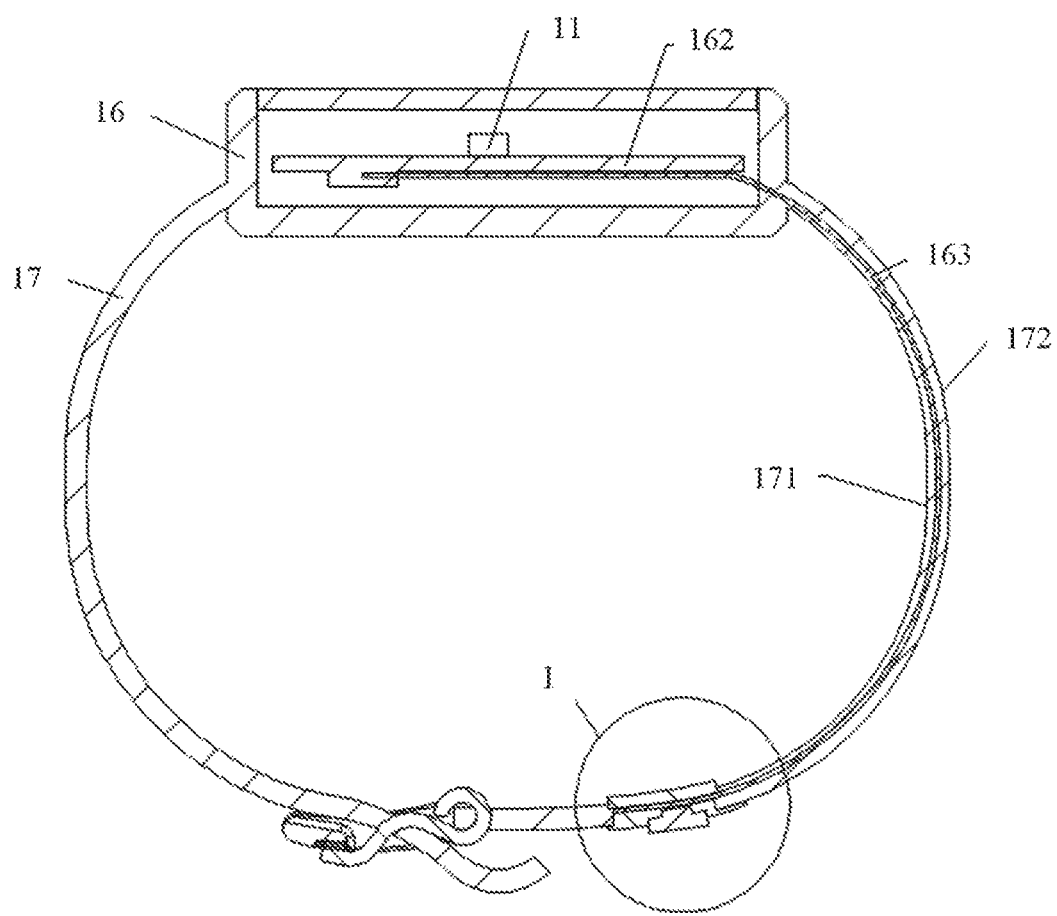
FIG. 20 is a sectional view of a structure of the smartwatch shown in FIG. 18 in an H-H position.
Figure 21:
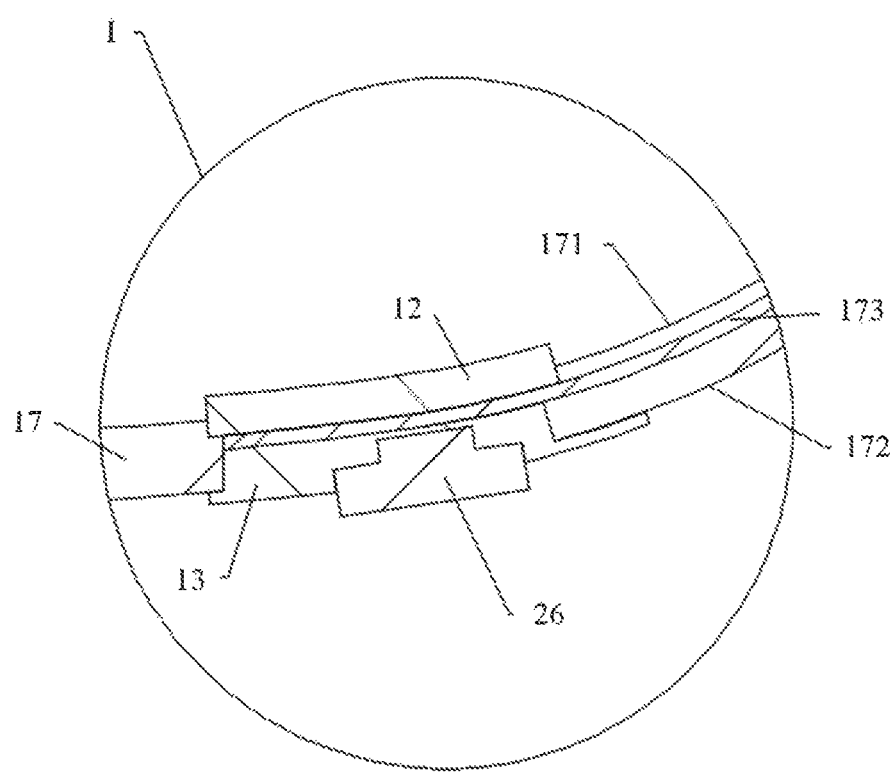
FIG. 21 is an enlarged schematic diagram of a structure in a position I in FIG. 20.

Optionally, the bottom wall 1611 includes a central region 1617 and a peripheral region 1618 disposed around a periphery of the central region 1617. The inner electrode 12 is disposed in the peripheral region 1618. The inner electrode 12 may be a complete ring (as shown in FIG. 13), or may be a plurality of arc-shaped segments that are alternately disposed (as shown in FIG. 17). When the inner electrode 12 is a plurality of arc-shaped segments, the plurality of arc-shaped segments may be symmetrically disposed and are slightly higher than a region that is in the peripheral region 1618 and in which no arc-shaped segment is arranged, to improve reliability of being in contact with the first wearing position 200 by the inner electrode 12.

The bottom wall 1611 is disposed with a concave installation slot. The inner electrode 12 is built in the installation slot. A sealing ring may be disposed between an outer side face of the inner electrode 12 and a wall of the installation slot, to prevent moisture and dust from entering the housing 161 through the third through hole 1614'.

Optionally, the outer electrode 13 includes a touch portion 131 and a fixing portion 132 connected to the touch portion 131. The touch portion 131 is configured to be touched by the non-wearing position 300, so as to collect the electric potential signal of the non-wearing position 300. The fixing portion 132 extends into the housing 161 to be connected to the end 1613. In this case, the fixing portion 132 may be stuck to the end 1613 by using a glue dispensing process or adhesive sticker at a connection joint.

The watch plate 16 further includes a third electrode spring 167', and the third electrode spring 167' is fastened to the connection circuit board 163' and is elastically connected to the fixing portion 132. The outer electrode 13 is electrically connected to the circuit board 162 sequentially by using the third electrode spring 160' and the connection circuit board 163', thereby being electrically connected to the electrocardiosignal collection circuit 11.

Referring to FIG. 1 to FIG. 17, in an optional embodiment, the central region 1617 is disposed with a detection window 181 and a transparent lens 182 covering the detection window 181. The detection window 181 may be disposed between the at least two inner electrodes 12, so that a structure of the central region 1617 is more compact. The watch plate 16 further includes a photoplethysmogram (PPG) 18 disposed inside the housing 161. The photoplethysmogram 18 is configured to detect a heart rate of the user through the detection window 181. Because the detection window 181 is disposed on the bottom wall 1611 of the housing 161, the detection window 181 continuously directly faces the first wearing position 200, and the smartwatch 100 can continuously detect the heart rate of the user.

The watch plate 16 further includes a sensor chip. The sensor chip is electrically connected to the photoplethysmogram 18 and the processing chip 14, and is configured to transmit, to the processing chip 14, heart rate data of the user defected by the photoplethysmogram 18. The processing chip 14 calculates and corrects a time difference between the electrocardiosignal data and the heart rate data based on the electrocardiosignal data and the heart rate data, to obtain a blood pressure value of the user. The smartwatch 100 can continuously detect the electrocardiosignal data and the heart rate data, and therefore, can continuously detect a fluctuation of blood pressure, to discover a problem of a blood pressure abnormality (for example, a common disease such as hypertension of people) in time, and can detect a health status of blood vessels (for example, vascular elasticity, a degree of vascular sclerosis, or whether a blood vessel is blocked).

Referring to FIG. 18 to FIG. 21, in an optional embodiment, the watch band 17 includes an inner side 171 and an outer side 172 that are disposed opposite to each other. The inner side 171 is configured to be in contact with the first wearing position 200. The inner electrode 12 is disposed on the inner side 171. The outer electrode 13 is disposed on the outer side 172. The watch band 17 is disposed with a second flexible circuit board 173. The inner electrode 12 and the outer electrode 13 are electrically connected to the circuit board 162 by using the second flexible circuit board 173, thereby being electrically connected to the electrocardiosignal collection circuit 11.

In this embodiment, the inner electrode 12 and the outer electrode 13 are fastened to the watch band 17, to simplify an inner structure of the watch plate 16, thereby reducing a size of the watch plate 16. This is beneficial to miniaturization of the smartwatch 100.

Optionally, the second flexible circuit board 173 is disposed inside the watch band 17. When the smartwatch 100 is being manufactured, the inner electrode 12 and the outer electrode 13 may be first welded to the second flexible circuit board 173 in advance, and then the second flexible circuit board 173 is buried in the watch band 17 in advance by using an insert injection process or a thermal compression silica gel process, thereby satisfying requirements of reliable fastening and water resistance. The outer electrode 13 and the inner electrode 12 may be respectively fastened on two opposite sides of the second flexible circuit board 173, to simplify a manufacturing process of the smartwatch 100.

In another implementation, the second flexible circuit board 173 may be alternatively attached to the inner side 171 of the watch band 17.

Optionally, the second flexible circuit board 173 and the circuit board 162 may be connected by using a ZIF connector or a BIB connector.

Referring to FIG. 1 to FIG. 4 and FIG. 18 to FIG. 22, in an optional embodiment, the fittings 2 of the smartwatch 100 include a fixing band 22, a connector (25/26), and a cable 23 connected between the fixing band 22 and the connector (25/26). The detection electrode 21 is disposed on an inner side of the fixing band 22. The fixing band is 22 configured to fasten the detection electrode 21 to the second wearing position 400. One end of the cable 23 is electrically connected to the detection electrode 21, and the other end of the cable 23 is electrically connected to a connection terminal (for example, an edge connector) of the connector (25/26). The connector (25/26) is detachably connected to the body 1.

In this embodiment, because the connector (25/26) is detachably connected to the body 1, a detachable connection relationship also exists between the fittings 2 and the body 1. The fittings 2 may be connected to the body 1 when continuous detection needs to be performed, and may be detached from the body 1 when no continuous detection needs to be performed, so as to reduce a weight of the smartwatch 100, thereby improving use flexibility of the smartwatch 100.

Optionally, the smartwatch 100 further includes a temperature detection electrode 24 fastened to the fixing band 22. The temperature detection electrode 24 is electrically connected to the connector (25/26) by using the cable 23. The temperature detection electrode 24 is configured to detect a body temperature of the user, so that the smartwatch 100 can simultaneously detect the body temperature of the user. The temperature detection electrode 24 is electrically connected to the processing chip 14. The processing chip 14 can display the body temperature of the user on the display 15.

Figure 4:
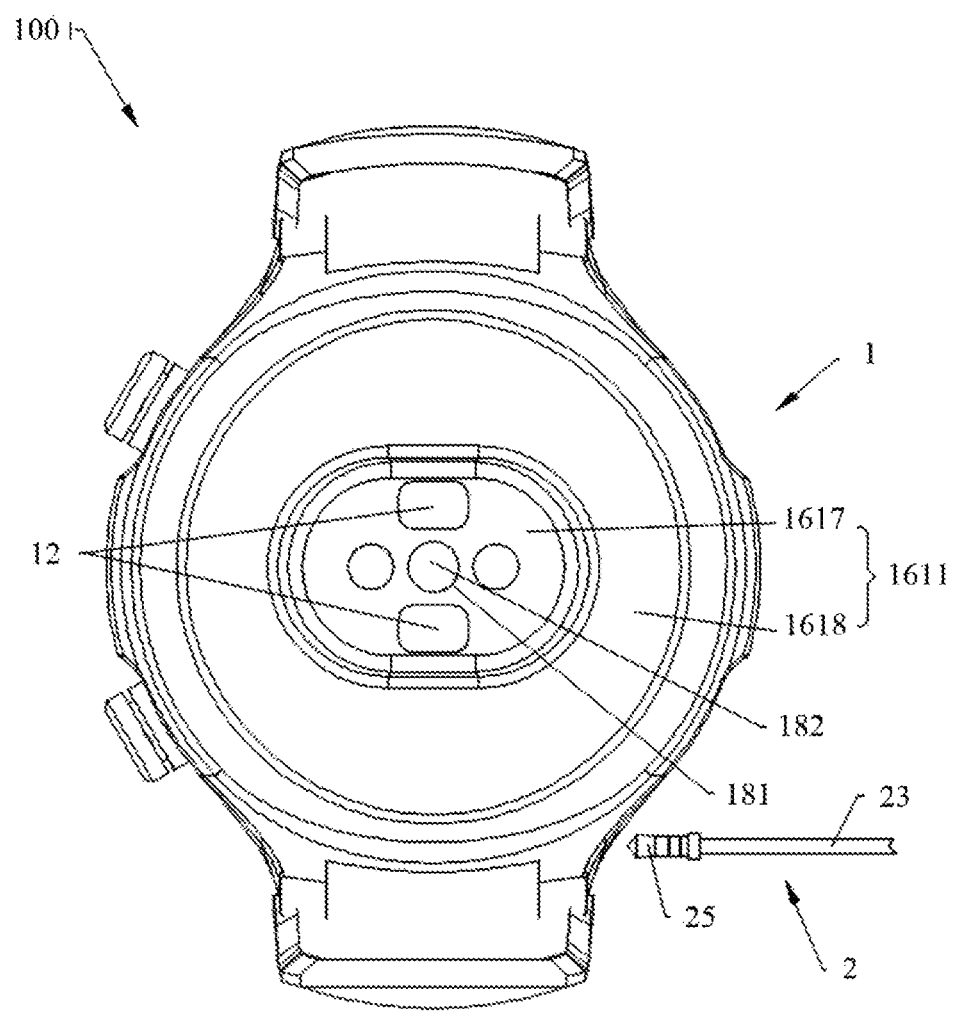
FIG. 4 is a bottom view of the smartwatch shown in FIG. 3.
Figure 22:
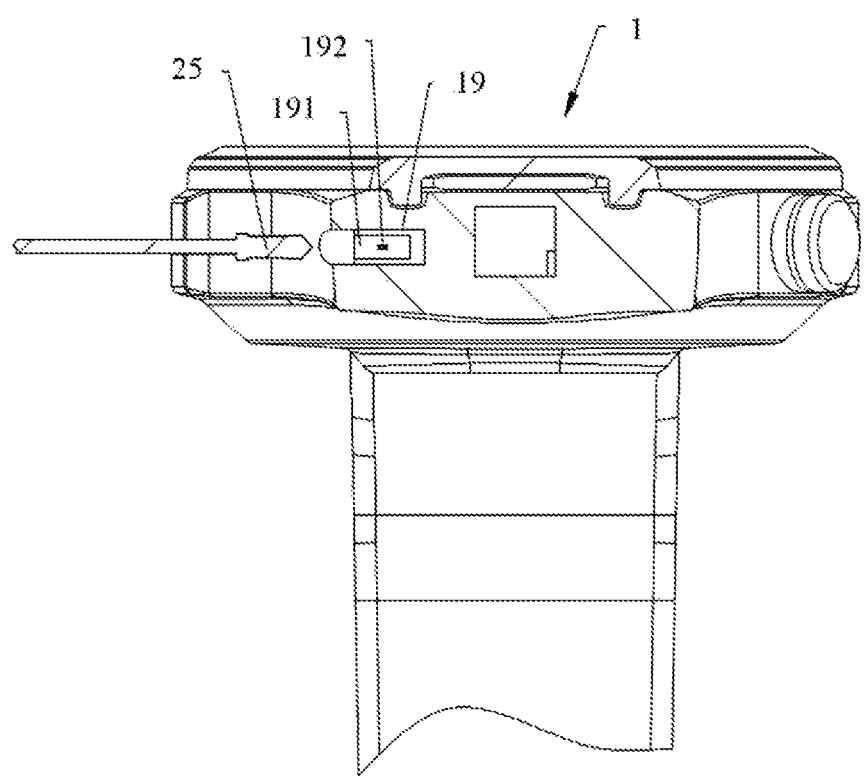
FIG. 22 is a sectional view of a structure of the smartwatch shown in FIG. 3 in an A-A position.

Referring to FIG. 3, FIG. 4, and FIG. 22, in an implementation, the connector is a plug 25. The body 1 is disposed with a socket 19 electrically connected to the electrocardiosignal collection circuit 11. The plug 25 is detachably connected to the socket 19. The plug 25 is connected to the socket 19 by using a plug-in structure.

Optionally, the socket 19 is disposed with a jack 191. A hole wall of the jack 191 is disposed with a spring 192. The spring 192 is configured to clamp the plug 25 inserted into the jack 191, so that the plug 25 can be stably plugged into the socket 19. In addition, the spring 192 also has an electrical connection function.

Optionally, the plug 25 is a USB (Universal Serial Bus, universal serial bus) plug or an earphone plug. The socket 19 is a USB socket or an earphone jack matching the plug 25.

Referring to FIG. 18 to FIG. 21, in another implementation, the connector is a magnetic head 26. The magnetic head 26 is detachably adsorbed on the outer electrode 13. Specifically, the outer electrode 13 is made of a metal material, and the magnetic head 26 is disposed with a magnet, so that the magnetic head 26 can be adsorbed on the outer electrode 125. The magnetic head 26 and the outer electrode 13 may be positioned by using a mortise and tenon connection (which is a connection manner for combining a mortise hole of one component and a tenon tongue of the other component).

In another implementation, the cable 23 of the fittings 2 may be a wire, a weave sleeve containing a conductive fiber, a nonwoven fabric containing a conductive fiber, a flexible film having a printed line, or the like. Forms are not limited, and similar connection manners shall all fall within the protection scope of this application. In this case, the connector may be a tab electrode. The detection electrode 21 may be a tab electrode. For example, the cable 23 is a weave sleeve containing a conductive fiber. The detection electrode 21 is a tab electrode fastened to one end of the weave sleeve, and the connector is a tab electrode fastened to the other end of the weave sleeve. The weave sleeve is worn on the arm on the wearing side of the user. The detection electrode 21 is attached to the second wearing position 400. The connector is attached to the body 1 to be electrically connected to the electrocardiosignal collection circuit 11, so that the electrocardiosignal collection circuit 11 can collect the electric potential signal of the second wearing position 400 by using the detection electrode 21.

In another implementation, the fittings 2 may not be configured with the connector, and the cable 23 is connected to the body 1. When the fittings 2 are not used, the fittings 2 may be accommodated in the housing 161. When the fittings 2 need to be used, the fixing band 22 is then taken out, and the cable 23 is extended, so that the detection electrode 21 can be fastened to the second wearing position 400.

In another implementation, the fittings 2 may not be configured with the cable 23, and the detection electrode 21 is connected to the body 1 by using a radio technology.

What is claimed is:

1. A smartwatch, comprising:
   a watch band;
   a watch plate coupled to the watch band and comprising:
      an electrocardiosignal collection circuit configured to obtain electrocardiosignal data of a user when the smartwatch is worn by the user;
      a housing comprising:
         a side wall comprising an end disposed with a groove; and
         a bottom wall coupled to the side wall and comprising:
            a central region comprising a detection window; and
            a peripheral region around the central region;
      a transparent lens covering the detection window;
      a processor electrically coupled to the electrocardiosignal collection circuit and configured to generate an electrocardiogram according to the electrocardiosignal data;
      a display electrically coupled to the processor and configured to display the electrocardiogram, wherein the display and the bottom wall are disposed opposite to each other, and wherein the side wall is positioned between the display and the bottom wall; and a photoplethysmogram apparatus disposed inside the housing, wherein the photoplethysmogram apparatus is configured to detect a heart rate of the user through the detection window when the smartwatch is worn by the user;

a first electrode electrically coupled to the electrocardiosignal collection circuit and disposed in the peripheral region, wherein the first electrode is configured to contact a first body part of the user when the smartwatch is worn by the user;

a second electrode electrically coupled to the electrocardiosignal collection circuit and disposed in the peripheral region, wherein the second electrode is configured to contact a second body part of the user when the smartwatch is worn by the user, wherein the first electrode and the second electrode are alternately disposed, and wherein the first electrode and the second electrode are arc-shaped segments and are positioned around the detection window; and a third electrode electrically coupled to the electrocardiosignal collection circuit and exposed to the side wall, wherein the third electrode is configured to contact a third body part of the user when the smartwatch is worn by the user, and wherein the third electrode comprises:
a touch portion configured to contact the third body part when the smartwatch is worn by the user; and
a fixing portion coupled to the touch portion, wherein the fixing portion extends into the housing, and wherein the fixing portion is engaged into the groove so that the third electrode is fastened to the housing, wherein a first surface of the first electrode or the second electrode protrudes above a second surface on which no electrode is arranged in the peripheral region, and wherein the watch plate further comprises:
an electrode spring coupled to the housing, wherein one end of the electrode spring extends into a groove to be coupled to the fixing portion; and
a flexible circuit board coupled to the housing, wherein another end of the electrode spring is coupled to a first end of the flexible circuit board, and wherein a second end of the flexible circuit board is electrically coupled to the electrocardiosignal collection circuit.

2. The smartwatch of claim 1, wherein the first electrode, the second electrode, and the third electrode are made of metal.

3. The smartwatch of claim 1, wherein the watch plate further comprises:
a first circuit board coupled to the housing, wherein the first circuit board is configured to couple to the electrocardiosignal collection circuit and includes a first through hole;
a fixed circuit board electrically coupled to the first circuit board, wherein the fixed circuit board comprises:
a second through hole;
a pad located on a periphery of the second through hole;
an electrode sheet coupled to the first electrode;
a connection base coupled to the electrode sheet; and
a screw coupled to the connection base, wherein the connection base extends into the first through hole, and wherein the screw is coupled to the connection base after passing through the second through hole such that the connection base is in contact with the pad.

4. The smartwatch of claim 3, wherein the pad comprises:
a first subpad disposed on a side of the fixed circuit board and in contact with the connection base; and
a second subpad coupled to the first subpad, wherein the first subpad and the second subpad are disposed opposite to each other, wherein the second subpad is disposed on a side of the fixed circuit board away from the connection base, wherein the second subpad is in contact with the screw, and wherein the screw is made of a conductive material.

5. The smartwatch of claim 3, wherein the watch plate further comprises:
a flexible circuit board coupled to the housing;
an electrode spring disposed inside the housing; and
a connection circuit board coupled to the housing and electrically coupled to the flexible circuit board,
wherein the first electrode is located on an outer side of the bottom wall,
wherein the bottom wall further comprises a third through hole, and
wherein the electrode spring passes through the third through hole and is pressed between the first electrode and the connection circuit board.

6. The smartwatch of claim 1, wherein the third electrode is ring-shaped.

7. The smartwatch of claim 6, wherein an outer diameter of the third electrode is greater than an outer diameter of the display.

8. The smartwatch of claim 1, wherein the at least the portion of the display is disposed between the at least the portion of the third electrode and at least a portion of the side wall.

9. A smartwatch, comprising:
a watch band;
a watch plate coupled to the watch band and comprising:
an electrocardiosignal collection circuit configured to obtain electrocardiosignal data of a user when the smartwatch is worn by the user;
a housing comprising:
a side wall; and
a bottom wall coupled to the side wall and comprising:
a central region comprising a detection window; and
a peripheral region around the central region;
a first circuit board coupled to the housing, wherein the first circuit board is configured to couple to the electrocardiosignal collection circuit and includes a first through hole;
a transparent lens covering the detection window;
a processor electrically coupled to the electrocardiosignal collection circuit and configured to generate an electrocardiogram according to the electrocardiosignal data;
a display electrically coupled to the processor and configured to display the electrocardiogram, wherein the display and the bottom wall are disposed opposite to each other, and wherein the side wall is positioned between the display and the bottom wall; and
a photoplethysmogram apparatus disposed inside the housing, wherein the photoplethysmogram apparatus is configured to detect a heart rate of the user through the detection window when the smartwatch is worn by the user;
a first electrode electrically coupled to the electrocardiosignal collection circuit and disposed in the peripheral region, wherein the first electrode is configured to contact a first body part of the user when the smartwatch is worn by the user;
a second electrode electrically coupled to the electrocardiosignal collection circuit and disposed in the peripheral region, wherein the second electrode is configured to contact a second body part of the user when the smartwatch is worn by the user, wherein the first electrode and the second electrode are alternately disposed, and wherein the first electrode and the second electrode are arc-shaped segments and are positioned around the detection window; and
a third electrode electrically coupled to the electrocardiosignal collection circuit and exposed to the side wall, wherein the third electrode is configured to contact a third body part of the user when the smartwatch is worn by the user,
wherein a first surface of the first electrode or the second electrode protrudes above a second surface on which no electrode is arranged in the peripheral region,
wherein the watch plate further comprises a fixed circuit board electrically coupled to the first circuit board, and wherein the fixed circuit board comprises:
a second through hole;
a pad located on a periphery of the second through hole;
an electrode sheet coupled to the first electrode;
a connection base coupled to the electrode sheet; and
a screw coupled to the connection base, wherein the connection base extends into the first through hole, and wherein the screw is coupled to the connection base after passing through the second through hole such that the connection base is in contact with the pad.

10. The smartwatch of claim 9, wherein the third electrode comprises:
a touch portion configured to contact the third body part of the user when the smartwatch is worn by the user; and
a fixing portion coupled to the touch portion, wherein the fixing portion extends into the housing.

11. The smartwatch of claim 9, wherein the first electrode, the second electrode, and the third electrode are made of metal.

12. The smartwatch of claim 9, wherein the pad comprises:
a first subpad disposed on a side of the fixed circuit board and in contact with the connection base; and
a second subpad coupled to the first subpad, wherein the first subpad and the second subpad are disposed opposite to each other, wherein the second subpad is disposed on a side of the fixed circuit board away from the connection base, wherein the second subpad is in contact with the screw, and wherein the screw is made of a conductive material.

13. The smartwatch of claim 9, wherein the third electrode comprises a fixing portion, and wherein the watch plate further comprises:
an electrode spring coupled to the housing, wherein one end of the electrode spring extends into a groove to be coupled to the fixing portion; and
a flexible circuit board coupled to the housing, wherein another end of the electrode spring is coupled to a first end of the flexible circuit board, and wherein a second end of the flexible circuit board is electrically coupled to the electrocardiosignal collection circuit.

14. The smartwatch of claim 9, wherein the watch plate further comprises:
a flexible circuit board coupled to the housing;
an electrode spring disposed inside the housing; and
a connection circuit board coupled to the housing and electrically coupled to the flexible circuit board,
wherein the first electrode is located on an outer side of the bottom wall,
wherein the bottom wall further comprises a third through hole, and
wherein the electrode spring passes through the third through hole and is pressed between the first electrode and the connection circuit board.

15. The smartwatch of claim 9, wherein the third electrode is ring-shaped.

16. The smartwatch of claim 15, wherein an outer diameter of the third electrode is greater than an outer diameter of the display.

17. The smartwatch of claim 9, wherein at least a portion of the display is positioned between at least a portion of the third electrode and the bottom wall.

18. The smartwatch of claim 17, wherein the at least the portion of the display is disposed between the at least the portion of the third electrode and at least a portion of the side wall.

19. A smartwatch, comprising:
a watch band;
a watch plate coupled to the watch band and comprising:
an electrocardiosignal collection circuit configured to obtain electrocardiosignal data of a user when the smartwatch is worn by the user;
a housing comprising:
a side wall; and
a bottom wall coupled to the side wall and comprising:
a central region comprising a detection window; and
a peripheral region around the central region;
a transparent lens covering the detection window;
a processor electrically coupled to the electrocardiosignal collection circuit and configured to generate an electrocardiogram according to the electrocardiosignal data;
a display electrically coupled to the processor and configured to display the electrocardiogram, wherein the display and the bottom wall are disposed opposite to each other, and wherein the side wall is positioned between the display and the bottom wall; and
a photoplethysmogram apparatus disposed inside the housing, wherein the photoplethysmogram apparatus is configured to detect a heart rate of the user through the detection window when the smartwatch is worn by the user;
a first electrode electrically coupled to the electrocardiosignal collection circuit and disposed in the peripheral region, wherein the first electrode is configured to contact a first body part of the user when the smartwatch is worn by the user;
a second electrode electrically coupled to the electrocardiosignal collection circuit and disposed in the peripheral region, wherein the second electrode is configured to contact a second body part of the user when the smartwatch is worn by the user, wherein the first electrode and the second electrode are alternately disposed, and wherein the first electrode and the second electrode are arc-shaped segments and are positioned around the detection window; and a third electrode that comprises a fixing portion, that is electrically coupled to the electrocardiosignal collection circuit, and that is exposed to the side wall, wherein the third electrode is configured to contact a third body part of the user when the smartwatch is worn by the user, wherein a first surface of the first electrode or the second electrode protrudes above a second surface on which no electrode is arranged in the peripheral region, and wherein the watch plate further comprises:
 a first electrode spring coupled to the housing, wherein one end of the first electrode spring extends into a groove to be coupled to the fixing portion; and
 a flexible circuit board coupled to the housing, wherein another end of the first electrode spring is coupled to a first end of the flexible circuit board, and wherein a second end of the flexible circuit board is electrically coupled to the electrocardiosignal collection circuit.

20. The smartwatch of claim 19, wherein the third electrode comprises a touch portion configured to contact the third body part of the user when the smartwatch is worn by the user, and wherein the fixing portion is coupled to the touch portion and extends into the housing.

21. The smartwatch of claim 19, wherein the first electrode, the second electrode, and the third electrode are made of metal.

22. The smartwatch of claim 19, wherein the watch plate further comprises:
 a first circuit board coupled to the housing, wherein the first circuit board is configured to couple to the electrocardiosignal collection circuit and includes a first through hole;
 a fixed circuit board electrically coupled to the first circuit board, wherein the fixed circuit board comprises:
  a second through hole;
  a pad located on a periphery of the second through hole;
  an electrode sheet coupled to the first electrode;
  a connection base coupled to the electrode sheet; and
  a screw coupled to the connection base, wherein the connection base extends into the first through hole, and wherein the screw is coupled to the connection base after passing through the second through hole such that the connection base is in contact with the pad.

23. The smartwatch of claim 22, wherein the pad comprises:
 a first subpad disposed on a side of the fixed circuit board and in contact with the connection base; and
 a second subpad coupled to the first subpad, wherein the first subpad and the second subpad are disposed opposite to each other, wherein the second subpad is disposed on a side of the fixed circuit board away from the connection base, wherein the second subpad is in contact with the screw, and wherein the screw is made of a conductive material.

24. The smartwatch of claim 22, wherein the watch plate further comprises:
 a second electrode spring disposed inside the housing; and
 a connection circuit board coupled to the housing and electrically coupled to the flexible circuit board,
 wherein the first electrode is located on an outer side of the bottom wall,
 wherein the bottom wall further comprises a third through hole, and
 wherein the second electrode spring passes through the third through hole and is pressed between the first electrode and the connection circuit board.

25. The smartwatch of claim 19, wherein at least a portion of the display is positioned between at least a portion of the third electrode and the bottom wall.

* * * * *